(12) United States Patent
Ariizumi et al.

(10) Patent No.: US 12,338,445 B2
(45) Date of Patent: Jun. 24, 2025

(54) FRUIT-BEARING PLANT EXHIBITING HIGH TEMPERATURE RESISTANCE, HIGH YIELD, AND PARTHENOCARPY

(71) Applicant: UNIVERSITY OF TSUKUBA, Tsukuba (JP)

(72) Inventors: Tohru Ariizumi, Tsukuba (JP); Hiroshi Ezura, Tsukuba (JP); Keiichiro Harada, Tsukuba (JP); Yoshihito Shinozaki, Tsukuba (JP); Ryoichi Yano, Tsukuba (JP); U Riku, Tsukuba (JP)

(73) Assignee: UNIVERSITY OF TSUKUBA, Tsukuba (JP)

( * ) Notice: Subject to any disclaimer, the term of this patent is extended or adjusted under 35 U.S.C. 154(b) by 532 days.

(21) Appl. No.: 17/638,572

(22) PCT Filed: Aug. 28, 2020

(86) PCT No.: PCT/JP2020/032724
§ 371 (c)(1),
(2) Date: Feb. 25, 2022

(87) PCT Pub. No.: WO2021/040011
PCT Pub. Date: Mar. 4, 2021

(65) Prior Publication Data
US 2022/0298524 A1    Sep. 22, 2022

(30) Foreign Application Priority Data

Aug. 30, 2019 (JP) .................................. 2019-158950

(51) Int. Cl.
*C12N 15/82* (2006.01)
*C07K 14/415* (2006.01)
*C12Q 1/6895* (2018.01)

(52) U.S. Cl.
CPC ........ *C12N 15/8262* (2013.01); *C07K 14/415* (2013.01); *C12Q 1/6895* (2013.01); *C12Q 2600/13* (2013.01); *C12Q 2600/158* (2013.01)

(58) Field of Classification Search
CPC ............................................... C12N 15/8262
USPC ....................................................... 800/289
See application file for complete search history.

(56) References Cited

U.S. PATENT DOCUMENTS

| 6,127,179 | A | * | 10/2000 | DellaPenna | ........ | C12N 15/8235 800/317.4 |
| 10,349,611 | B2 | | 7/2019 | Ezura et al. | | |
| 10,385,357 | B2 | | 8/2019 | Ezura et al. | | |
| 11,091,773 | B2 | | 8/2021 | Fukuoka et al. | | |
| 2016/0264989 | A1 | | 9/2016 | Ezura et al. | | |
| 2017/0002376 | A1 | | 1/2017 | Fukuoka et al. | | |
| 2017/0292130 | A1 | | 10/2017 | Ezura et al. | | |
| 2019/0110420 | A1 | | 4/2019 | Ezura et al. | | |
| 2019/0194684 | A1 | | 6/2019 | Nunome et al. | | |

FOREIGN PATENT DOCUMENTS

| JP | 2010-532164 A | 10/2010 |
| JP | 2015/089368 A | 5/2015 |
| JP | WO2014/021398 A1 | 7/2016 |
| JP | WO2017 /022859 A | 2/2017 |
| JP | WO2015/108185 A1 | 3/2017 |
| JP | WO2016/047778 A1 | 7/2017 |
| JP | 2019/013177 | 1/2019 |
| JP | 2019/013177 A | 1/2019 |
| WO | WO 99/21411 A1 | 5/1999 |
| WO | WO 2009/005343 A1 | 1/2009 |
| WO | WO 2017/022859 A1 | 2/2017 |

OTHER PUBLICATIONS

Okabe, Y., et al., "Tomato Tilling Technology: Development of a Reverse Genetics Tool for the Efficient Isolation of Mutants from Micro-Tom Mutant Libraries," *Plant Cell Physiol.*, 52(11):1994-2005 (2011).

Okabe, Y., et al., "Availability of Micro-Tom mutant library combined with Tilling in molecular breeding of tomato fruit shelf-life," *Breeding Science*, 62:202-208 (2012).

Shinozaki, Y., et al., "Ethylene suppresses tomato (*Soianum lycopersicum*) fruit set through modification of gibberellin metabolism," *The Plant Journal*, 83:237-251 (2015).

Written Opinion of the International Searching Authority issued for PCT/JP2020/032724, mailed Sep. 29, 2020.

International Search Report issued for PCT/JP2020/032724, mailed Sep. 29, 2020 (in Japanese; English translation included).

Database Genbank [online], Aug. 8, 2018 uploaded, [retrieved on Sep. 10, 2020], retrieved from the Internet: <URL: https://www.ncbi.nlm.nih.gov/nuccore/NC_015447.3?report=genbank&from=20373025&to=20374378>, Definition: Solanum lycopersicum cultivar Heinz 1706 chromosome 10, SL3.0, whole genome shotgun sequence., accession No. NC_015447, entire text.

(Continued)

*Primary Examiner* — Li Zheng
(74) *Attorney, Agent, or Firm* — Crowell & Moring LLP

(57) ABSTRACT

The present application provides: a fruit-bearing plant exhibiting parthenocarpy or a portion thereof including a mutation in a Solyc10g038170 gene or ortholog thereof, the mutation causing deficiency or reduction in expression of a protein encoded by the Solyc10g038170 gene or ortholog thereof; a method for producing a parthenocarpic fruit-bearing plant or a portion thereof; and a method for selecting a parthenocarpic fruit-bearing plant or a portion thereof.

9 Claims, 14 Drawing Sheets
Specification includes a Sequence Listing.

(56) References Cited

OTHER PUBLICATIONS

Written Opinion of the International Searching Authority issued for PCT/JP2020/032724, mailed Sep. 10, 2020.
Notice of Reasons for Refusal and Record of the Result of Prior Art Search received in Japanese Application No. 2021-543076, in Japanese and including English translation, mailed Apr. 23, 2024 (11 pages).
Harada, K., et al., "Searching Novel Parthenocarpic Genes in Tomato from the EMS Mutagenesis Line," Abstracts of Research Presentations and Symposium Lectures for the 2018 Fall Meeting of the Japanese Society for Horticultural Science, *Horticultural Research*, 17(2), in Japanese and including English translation, 8 pages (2018).

\* cited by examiner

| Strain | Parthenocarpic gene genotype | The number of emasculated flowers | The number of fructified plants | The number of non-fructified plants | Fructification rate (%) |
|---|---|---|---|---|---|
| 'Micro-Tom' WT | +/+ | 77 | 3 | 74 | 3.9 |
| BC₂S₂ P | m/m | 63 | 12 | 51 | 19.0 |

| Strain | Parthenocarpic gene genotype | The number of emasculated flowers | The number of fructified plants | The number of non-fructified plants | Fructification rate (%) |
|---|---|---|---|---|---|
| 'Micro-Tom' WT | +/+ | 45 | 0 | 45 | 0.0 |
| BC₃S₂ NP | +/+ | 41 | 4 | 37 | 9.8 |
| BC₃S₂ P | m/m | 59 | 5 | 54 | 8.5 |

FIG. 1

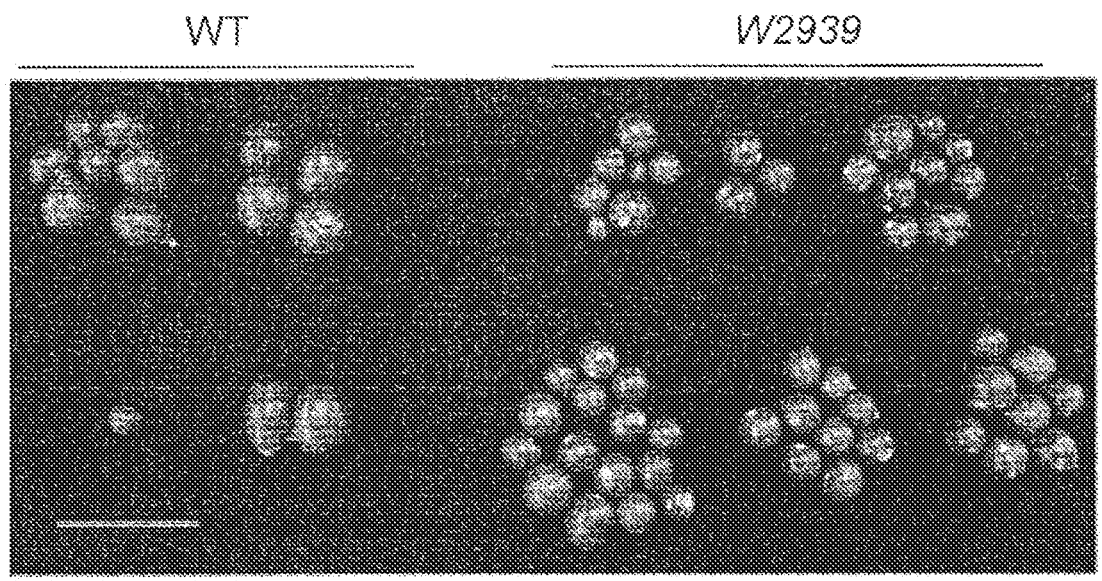
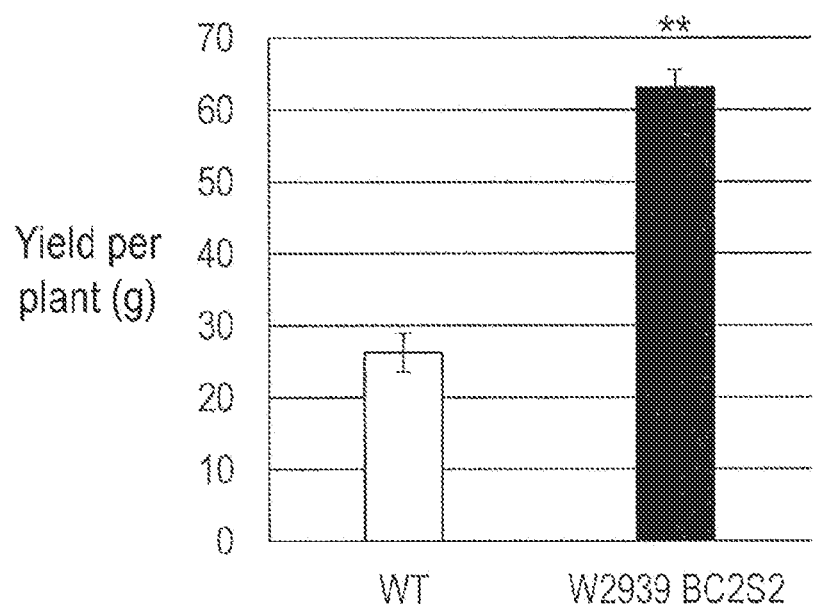
FIG. 2

| Marker name | Chromosome | Arm | Forward primer | SEQ ID NO: | Reverse primer | SEQ ID NO: |
|---|---|---|---|---|---|---|
| 6172_1047 | 1 | S | TTGGAGTAAACATGGCACTGA | 29 | AACCAAAACTGGTGCAGCATT | 30 |
| 273_877 | 1 | L | ATTGGGCTACTTCAGGTGGAAAATA | 31 | TCCGTGGTGCTTGTTTATAAACTTC | 32 |
| 7111_1701 | 2 | S | GTTTCAACCAAACAAATCCAATG | 33 | CAATGAAGTACCTGTGACAAATGC | 34 |
| 9673_646 | 2 | L | GCCGTAAATTGTTGACGAAA | 35 | GTAACTCCCAAGTCAGCATCA | 36 |
| 3351_2089 | 3 | S | GGAATGAATGGAGGGTATGGATGAT | 37 | GTCTCTCCTCAATACATCCCTTCA | 38 |
| 43_1626 | 3 | L | TCAACTGTAAAAGGTTCTCGTTG | 39 | TATCAACACTTCTTAGCTGCCTCT | 40 |
| 6649_455 | 4 | S | TAGGTATAGCCAGGAAGAGAA | 41 | GCCATATAGATCTTTAAGCTTGGCC | 42 |
| 837_663 | 4 | L | TCTAGCCTGTATTGCTGACTGTAAG | 43 | TCAGTATAGGACAAGACGGAAACC | 44 |
| 7138_174 | 5 | S | AAATGTTGCGTTATCTTGGCG | 45 | ATTCGTGAAGCCAGTTTCTAG | 46 |
| 9768_1494 | 5 | L | TCAGGGATTTGGATGGGAAAGA | 47 | TTCCATGCCCTTTTAAGCCAGTT | 48 |
| 7100_120 | 6 | S | GCATCTAAACGAGCTAAAAGGTAC | 49 | CCAAAACGAAGAAGTGATTGTGTTG | 50 |
| 6651_568 | 6 | L | TGTCCCTGTCATCCTGTATTTGGA | 51 | ACATGTTCAATGTTAGGCTGCA | 52 |
| 9024_376 | 7 | S | TTTCACTGTTGTTTCTTCCCTGA | 53 | GTCCACGACACGCGGCTAGAAT | 54 |
| 2971_740 | 7 | L | ATGAGGAGAAGTCAGAAGAAGCT | 55 | TGGATCCTCAGAAGCATCATGG | 56 |
| 10489_192 | 8 | S | GCCATAACTCTGCCCTTTGTTC | 57 | CGAACAATTAAACCTGAGGCA | 58 |
| 3528_593 | 8 | L | CAACCAAGAAACCCTTCAGCAG | 59 | ACAAACGATTGGGTCATGGAGA | 60 |
| 16586_441 | 9 | S | GGATCCTGCTTGTGTTTTTGCT | 61 | CTCCTCTTTGGCGGTTAAGAGT | 62 |
| 2910_740 | 9 | L | AGGCTCATCCCTTGTGTTCTGT | 63 | TTGTGTCCATGAACATGCTCTG | 64 |
| 2120_1008 | 10 | S | CAGAGGAGTTTGTGCAACAG | 65 | TCTCCACCCTCATTTCCCATC | 66 |
| 13536_438 | 10 | L | ACCAGAGAGAAGCAACAAGGA | 67 | TCTACCCACAAGACTAACTCGA | 68 |
| 2874_1225 | 11 | S | CACGATACGAGCAACAAATCC | 69 | GTTCCCACTTCTCAGAGCATCA | 70 |
| 18095_307 | 11 | L | ATGCTCAAAGGTACAAGGCTT | 71 | ACACACATTTTTGCAACTGCCA | 72 |
| 9542_306 | 12 | S | AAGCAGTTGATTGGTGGTGTATTC | 73 | CCATAAGAGCAGCTTCAAGAATCTG | 74 |
| 2559_638 | 12 | L | TCAGTGGTAAGTCCGTCTTTAACT | 75 | TGGAAAAGAGAGGAGATCCACTTT | 76 |

FIG. 5

| Marker name | Chr. | Arm | MT | RE | 1 | 2 | 3 | 4 | 5 | 6 | 7 | 8 | 9 | 10 | 11 | 12 | Frequency of M (%) |
|---|---|---|---|---|---|---|---|---|---|---|---|---|---|---|---|---|---|
| 6172_1047 | 1 | S | M | R | R | M | M | M | R | R | M | H | M | H | H | M | 50.0 |
| 273_977 | 1 | L | M | R | R | H | H | H | R | R | H | H | H | H | H | H | 8.3 |
| 7105_1701 | 2 | S | M | R | R | R | R | R | R | R | R | H | R | M | M | M | 25.0 |
| 9673_646 | 2 | L | M | R | R | R | H | R | R | M | H | R | R | H | H | M | 8.3 |
| 3351_2089 | 3 | S | M | R | H | H | M | H | H | M | H | H | M | H | H | M | 25.0 |
| 43_1626 | 3 | L | M | R | H | H | H | H | H | R | R | R | H | R | H | M | 25.0 |
| 6643_455 | 4 | S | M | R | H | R | M | M | M | M | M | H | R | H | H | R | 33.3 |
| 837_663 | 4 | L | M | R | H | H | H | H | H | R | H | H | R | H | H | H | 8.3 |
| 7138_174 | 5 | S | M | R | H | M | M | M | M | R | M | M | H | M | M | M | 50.0 |
| 9768_1494 | 5 | L | M | R | R | M | H | H | H | R | R | R | H | H | R | H | 50.0 |
| 7100_120 | 6 | S | M | R | H | R | R | R | M | H | H | H | M | H | H | H | 8.3 |
| 6651_568 | 6 | L | M | R | R | H | H | H | R | R | M | M | R | M | R | R | 25.0 |
| 9024_376 | 7 | S | M | R | M | M | M | H | R | M | M | H | M | H | H | H | 16.7 |
| 2971_740 | 7 | L | M | R | H | H | H | H | R | R | H | R | M | H | H | M | 33.3 |
| 10489_192 | 8 | S | M | R | H | H | H | M | M | M | H | H | H | H | R | H | 16.7 |
| 3538_583 | 8 | L | M | R | M | M | R | R | R | R | H | R | H | M | R | R | 41.7 |
| 16586_441 | 9 | S | M | R | H | M | H | H | H | M | H | M | R | H | M | H | 33.3 |
| 2910_740 | 9 | L | M | R | H | H | H | H | M | M | H | M | H | H | H | M | 33.3 |
| 2120_1008 | 10 | S | M | R | M | M | M | M | M | M | M | M | M | M | M | M | 83.3 |
| 13536_433 | 10 | L | M | R | H | H | M | M | M | M | M | M | M | M | M | M | 66.7 |
| 2874_1225 | 11 | S | M | R | R | M | M | M | R | M | H | M | H | M | M | M | 66.7 |
| 18093_307 | 11 | L | M | R | R | H | M | M | M | H | H | H | H | H | H | M | 33.3 |
| 9542_306 | 12 | S | M | R | H | M | M | M | R | M | M | M | M | M | M | M | 58.3 |
| 2559_638 | 12 | L | M | R | H | H | R | M | H | M | H | M | H | H | M | M | 25.0 |

FIG. 6

```
                                 20                            40
                                  |                             |
Solyc10g038170    MPSFSGQSPE  KIGKNWMEYQ  GIKNWEGLLD  PLDDNIRGEI  40
   At2G44810      M---------  -------EYQ  GLQNWDGLLD  PLDDNIRREI  24

60                            80
                                  |                             |
Solyc10g038170    IRYGHFVEAA  YRACNFDPSS  PSYAMCKYSR  KKLFHLSGFS  80
   At2G44810      LRYGQFVESA  YQAFDFDPSS  PTYGTCRFPR  STLLERSGLP  64
```

| Strain | Sequence (5' → 3') | SEQ ID NO: | Editing pattern | The number of amino acid residues |
|---|---|---|---|---|
| WT | TTGATCCACTAGATGATGATAATTT--ACGTGGAGAAA | 14 | WT | 376 a.a. |
| #3-1 | TTGATCCACTAGATGATGATAATTTTACGTGGAGAAA | 15 | +1 | 47 a.a. |
| #9-1 | TTGATCCACTAGATGATGATAATTT--ACGTGGAGAAA<br>TTGATCCACTAGATGATGATAATTTTACGTGGAGAAA | 14<br>15 | WT / +1 | — |
| #10-1 | TTGATCCACTAGATGATGATAATTT--ACGTGGAGAAA<br>TTGATCCACTAGATGATGATAATTTTACGTGGAGAAA | 14<br>15 | WT / +1 | — |
| #25-1 | TTGATCCACTAGATGATGATAATTTTACGTGGAGAAA<br>TTGATCCACTAGATGATGATAAT---ACGTGGAGAAA | 15<br>16 | +1 / -2 | 47/42 a.a. |
| #37-1 | TTGATCCACTAGATGATGATAATTT--ACGTGGAGAAA | 14 | WT / +1 | — |
| #42-1 | TTGATCCACTAGATGATGATAATTTTACGTGGAGAAA<br>TTGATCCACTAGATGATGATAAT---ACGTGGAGAAA | 15<br>16 | +1 / -2 | 47/42 a.a. |
| #9-3 | — | — | Chimera | — |
| #9-4 | — | — | Chimera | — |

FIG. 13

| Strain | Sequence | SEQ ID NO: | Mutation | Polypeptide length |
|---|---|---|---|---|
| WT | LDDNLRGEIIRYGHFVEAAY | 17 | - | 376 a.a. |
| W2939 | LDDNLCGEIIRYGHFVEAAY | 18 | Missense | 376 a.a. |
| #3-1 | LDDNFTWRNNSIWTFC* | 19 | Frameshift | 47 a.a. |
| #25-1 | LDDNFTWRNNSIWTFC* | 19 | Frameshift | 47 / 42 a.a. |
| | LDDNTRKNYSR* | 20 | | |
| #42-1 | LDDNFTWRNNSIWTFC* | 19 | Frameshift | 47 / 42 a.a. |
| | LDDNTRKNYSR* | 20 | | |

FIG. 14

FRUIT-BEARING PLANT EXHIBITING HIGH TEMPERATURE RESISTANCE, HIGH YIELD, AND PARTHENOCARPY

RELATED APPLICATIONS

The present application is § 371 filing based on International Application No. PCT/JP2020/032724, filed Aug. 28, 2020, which claims priority to Japanese Application No. 2019-158950, filed Aug. 30, 2019, the entireties of which are incorporated herein by reference.

Reference to Appendix [CD ROM/Sequence Listing] The instant application contains a Sequence Listing which has been submitted electronically in ASCII format and is hereby incorporated by reference in its entirety. Said ASCII copy, created on Aug. 28, 2020, is named "PH_8478_PCT_SequenceListing.txt" and is 61,954 bytes in size.

TECHNICAL FIELD

The present invention relates to a fruit-bearing plant exhibiting high temperature resistance, high yield, and parthenocarpy.

The present invention also relates to a method for producing the fruit-bearing plant exhibiting parthenocarpy.

The present invention further relates to a method for selecting a plant exhibiting parthenocarpy from fruit-bearing plants.

BACKGROUND ART

Although tomatoes are self-pollinating plants, it is known that the facility cultivation of tomato results in reduction in pollination and fructification rates due to lack of wind and insects which assist pollination. Therefore, methods for promoting parthenocarpy and fruit enlargement by plant hormone treatment of flower trusses are widely used. Alternatively, methods for promoting pollination using bumblebees or vibrators are also often used. However, plant hormone treatment and treatment for promoting pollination using vibrators require a lot of labor, which results in a significant decrease in labor efficiency. Although labor efficiency of a method using bumblebees is good, due to the limitation of the temperature range for activity of bumblebees, the method is problematic in that cost and effort for temperature control in a facility may increase during summer and winter. In addition, decrease of pollen fertility during summer and winter makes it difficult to secure stable fruit production throughout a year in the case of fructification via pollination/fertilization, which is also problematic. Therefore, to realize stable cultivation with reduced labor and cost while reducing influence of environmental factors such as seasonal factors, there is a demand for development of technology for inducing parthenocarpy in tomato plants at improved work efficiency.

A pat (e.g., pat-2) mutation, a s1del1a mutation, and the like are known as mutations inducing parthenocarpy in tomato plants (Patent Documents 1 to 3). In these techniques, a parthenocarpic mutation is introduced into another tomato strain using a parthenocarpic gene-linked DNA marker, thereby obtaining a tomato that produces seedless fruits.

Regarding still other mutations that induce parthenocarpy of tomato, a plant such as a parthenocarpic tomato plant having a mutant cyclin F-box gene is known (Patent Document 4).

Additionally, the production of a parthenocarpic plant by suppressing the function of parthenocarpy regulatory gene of Solanaceae plants is described in Patent Documents 5 and 6.

Furthermore, genetic mutations that impart heat tolerance into fruit-bearing its such as tomatoes are described in Patent Documents 7 and 8.

Regarding the parthenocarpy and mutation, it is described that Sletr1-1 and Sletr1-2 having mutations in the transmembrane region of the ethylene receptor protein ETR1 are effective in imparting shelf life and parthenocarpy (Non-Patent Documents 1 to 3).

CITATION LIST

Patent Document

Patent Document 1: WO 1999/021411 A1
Patent Document 2: WO 2017/022859 A1
Patent Document 3: JP 2010-532164 A
Patent Document 4: JP 2017/022859 A
Patent Document 5: JP 2014/021398 A
Patent Document 6: JP 2015/108185 A
Patent Document 7: JP 2015-089368 A
Patent Document 8: JP 2016/047778 A

Non-Patent Documents

Non-Patent Document 1: Okabe Y et al., Plant & Cell Physiology, 2011; 52 (11): 1994-2005
Non-Patent Document 2: Okabe Y et al., Breading Science, 2012; 62 (2): 202-208
Non-Patent Document 3: Shinozaki Y et al., The Plant Journal, 2015; 83 (2); 237-251

SUMMARY OF INVENTION

Technical Problem

The mutations described in Patent Documents 1 to 3 can increase the efficiency of parthenocarpy, but are known to have adverse effects on reproductive organs, vegetative organs, and the like, and reduce the quality of fruits.

It is an object of the present invention to provide a genetic mutation that can induce parthenocarpy highly efficiently, at least without causing any adverse effect on vegetative organs in plants of fruits including fruit trees or fruit vegetables.

Solution to Problem

As a result of diligent studies, the present inventors have found that a specific gene mutation can impart highly efficient parthenocarpy and high yield at a high temperature to fruity plants such as tomatoes, and this has led to the completion of the present invention.

Accordingly, the present invention encompasses the following characteristics.

[1] A fruit-bearing plant exhibiting parthenocarpy or a portion thereof including a mutation in a Solyc10g038170 gene or ortholog thereof, the mutation causing deficiency or reduction in expression of a protein encoded by the Solyc10g038170 gene or ortholog thereof.

[2] The fruit-bearing plant or a portion thereof according to [1], in which the gene or ortholog thereof is a polynucleotide encoding a protein including an amino acid sequence of SEQ ID NO: 2, or an amino acid sequence having 50% or greater sequence identity to the amino acid sequence.

[3] The fruit-bearing plant or a portion thereof according to [1] or [2], in which the mutation of the gene or ortholog thereof includes a nucleotide sequence encoding an amino acid sequence including a deletion, substitution, addition or insertion of at least one amino acid in the amino acid sequence of the protein.

[4] The fruit-bearing plant or a portion thereof according to [3], in which the substitution of at least one amino acid includes a substitution of arginine at 37 position in an amino acid sequence of SEQ ID NO: 2 with another amino acid.

[5] The fruit-bearing plant or a portion thereof according to [4], in which the substitution of at least one amino acid further includes a substitution of alanine at position 49 in the amino acid sequence of SEQ ID NO: 2 with another amino acid.

[6] The fruit-bearing plant or a portion thereof according to any one of [1] to [5], in which the fruit-bearing plant is selected from the group consisting of Solanaceae plants, Cucurbitaceae plants, Rosaceae plants, and Vitaceae plants.

[7] The fruit-bearing plant or a portion thereof according to any one of [1] to [6], including a parthenocarpic rate of 95% or greater, 96% or greater, 97% or greater, 98% or greater, or 99% or greater.

[8] The fruit-bearing plant or a portion thereof according to any one of [1] to [7], which is resistant to an ambient temperature of 30° C. or higher.

[9] The fruit-bearing plant or a portion thereof according to any one of [1] to [8], in which the fruit-bearing plant is homozygous for the mutation.

[10] A method for producing the fruit-bearing plant described in any one of [1] to [9]; including:
(1) introducing a mutation of a Solyc10g038170 gene or ortholog thereof into a cell, callus or tissue of a wild type of the plant; the mutation causing deficiency or reduction in expression of the Solyc10g038170 gene or ortholog thereof;
(2) culturing the cell, callus or tissue of the plan the step (1) to form a plant body population; and
(3) selecting a plant having parthenocarpy from the plant body population in the step (2).

[11] The method according to [10]; in which the mutation is a disruption or deficiency in the gene or ortholog thereof.

[12] The method according to [10]; in which the mutation is performed by introducing a polynucleotide including a mutation caused by a single base substitution, in a nucleotide sequence of SEQ ID NO: 1 of the Solyc10g038170 gene or a nucleotide sequence of ortholog of the gene, at a position or positions corresponding to position 109, position 146, or both position 109 and position 146 in a nucleotide sequence of SEQ ID NO: 1, or at a position in a nucleotide sequence of the ortholog corresponding to the position or positions.

[13] The method according to [12]; in which the polynucleotide includes a nucleotide sequence of SEQ ID NO: 3.

[14] The method according to any one of [10] to [13], in which the plant selected in the step (3) is homozygous for the mutation.

[15] A polynucleotide including a nucleotide sequence of SEQ ID NO: 3.

[16] A method for selecting a parthenocarpic plant from fruit-bearing plants, the method including detecting reduction or deficiency in expression of a Solyc10g038170 gene or ortholog thereof in a cell or tissue of the fruit-bearing plant, or a disruption or deficiency in the gene or ortholog thereof.

[17] The method according to [16], in which the detection is performed by PCR or hybridization.

The present specification includes a disclosure content of Japanese Patent Application No. 2019-158950 (filed on Aug. 30, 2019) on which priority of the present application is based.

The use of the mutation of the Solyc10g038170 gene or ortholog thereof according to the present invention can impart a high parthenocarpic rate of 99% or greater to tomatoes as fruit-bearing plants. Also, the induction of parthenocarpy can maintain high yields in a region where fructification is poor due to high temperatures. Furthermore, for example, gene modifying techniques such as genome editing and homologous recombination are used to induce similar mutations in the above-described gene or ortholog thereof, so that enhancement of parthenocarpy and high temperature resistance can be induced with high efficiency in any fruit-bearing plant.

BRIEF DESCRIPTION OF DRAWINGS

FIG. 1 shows the parthenocarpic rates of tomato Micro-Tom backcrossed strains. The figure above shows the parthenocarpic rates of the strains cultivated under high temperature stress conditions (in the summer). "P" indicates a parthenocarpic strain. 4 individuals of wild strain (WT) and 5 individuals of parthenocarpic strain were tested, and 11 to 20 flowers per individual were emasculated. The figure below shows the parthenocarpic rates of cultivated strains grown at a suitable growth temperature (24° C.). "NP" indicates a non-parthenocarpic strain, and "P" indicates a parthenocarpic strain. 3 individuals of wild strain and 4 individuals of $BC_3S_2$ strain were tested, and 10 to 15 flowers per individual were emasculated. Genotype indicates the genotypes of identified genetic mutations to be described later. "No. emasc" indicates the total number of emasculated flowers.

FIG. 2 shows the fruit yields of tomato W2939 BC2S2 parthenocarpic strain. Seeding of the BC2S2 strain and the Micro-Tom wild strain was carried out in May. The figure above shows the yields of red ripe fruits from late August to early September (4 individuals of Micro-Tom wild strain (WT) on the left, 6 individuals of W2939 BC2S2 parthenocarpic strain on the right). A bar indicates 5 cm. A column chart in the figure below shows the total yield of red ripe fruits per individual harvested from the middle of August to early October (n=6). Error bars indicate standard errors, and a symbol "**" indicates significant difference with wild strain (Student's t-test, 1% level).

FIGS. 3A and 3B show the number of seeds (n=6) contained in the red ripe fruits obtained from the Micro-Tom wild strain (A) and the W2939 BC2S2 parthenocarpic strain (B) Cultivation was carried out in a greenhouse under high temperature stress conditions (the observed daily average temperature was from about 25 to 33° C.). FIGS. 3C, 3D, and 3E show the number of seeds (C, E: n=8; D: n=5) contained in red ripe fruits obtained from the Micro-Tom wild strain (C), the BC3S2 non-parthenocarpic strain (D), and the W2939 BC3S2 parthenocarpic strain (E). Cultivation was carried out in a closed cultivation room at a constant temperature of 24° C. Numbers in each pie chart indicate the number of fruits.

FIGS. 4A and 4B show the measurement results of fruit weight and sugar content (fruit weight: WT, n=48; parthenocarpic strain, n=218, Brix: WT, n=37; parthenocarpic strain, n=98) in the Micro-Tom wild strain (WT) and the W2939 BC2S2 parthenocarpic strain. Each symbol "**" indicates that there is a significant difference from the wild strain (Welch's t-test, 1% level). Error bars indicate standard errors. FIGS. 4C and 4D show the measurement results of fruit weight and sugar content (fruit weight: WT, n=49; NP, n=38 SP, n=44, Brix: WT, n=48; NP, n=39; SP, n=37) in the Micro-Tom wild strain (WT), the W2939 BC3S2 non-parthenocarpic strain (NP), and the parthenocarpic strain (SP). The fruit weight has no significant difference between the strains (Tukey-Kramer, 5% level). Different alphabets indicate a significant difference between the strains (Tukey-Kramer, 1% level).

FIG. 5 shows a list of SNP markers used in rough mapping and primer sequences. Each marker name is based on the notation in the Tomato marker database. S denotes a short arm of a chromosome, and L denotes a long arm of a chromosome. Tomato chromosome numbers are shown for each chromosome.

FIG. 6 shows map-based cloning of W2939 strain using SNP markers. MT denotes a Micro-Tom wild strain, RE denotes a Regina wild strain, M denotes a Micro-Tom homozygous type, H denotes a heterozygous type, R denotes a Regina homozygous type, S denotes a chromosome short arm, and L denotes a chromosome long arm. Among $F_2$ hybrid strains produced by crossing the W2939 strain and the Regina, 12 individuals exhibiting parthenocarpy were used.

FIG. 8A shows mutation sites (as indicated by a comparison between W2939 and WT) in the nucleotide sequences (SEQ ID NOs: 5 and 6, respectively) at positions 1 to 150 of SEQ ID NO: 1 (wild type (WT)) and SEQ ID NO: 3 (W2939 (mutant)); and FIG. 8B shows mutation sites in amino acid sequences (SEQ ID NOs: 7 and 8) at positions 1 to 100 of SEQ ID NO: 2 (wild type (WT)) and SEQ ID NO: 4 (W2939 (mutant)), and each sequence site surrounded by a black frame indicates a mutation site. The mutation is a missense mutation in which arginine at position 37 (R) is replaced with cysteine (C) and alanine at position 49 (A) is replaced with valine (V).

FIG. 9 shows a comparison between the amino acid sequence of Solyc10g038170 (wild type) (at positions 1 to 80 of SEQ ID NO: 1; SEQ ID NO: 9) and the amino acid sequence of At2G-14810 (SEQ ID NO: 10), which is an Arabidopsis thaliana ortholog having the highest homology with the Solyc10g038170. Each sequence site surrounded by a black frame indicates a site where a missense mutation occurred in the W2939 strain (mutant).

FIG. 12 shows target sequences and base sequences around causative mutations (i.e., a base sequence from the translation start site of SEQ ID NO: 1 of Solyc10g038170 to 300 bp; SEQ ID NO: 11 (plus strand), and SEQ ID NO: 12 (complementary strand)) and an amino acid sequence (SEQ ID NO: 13). Two target sequences selected in Examples to be described later are indicated by a single line, the PAM sequence of each of the target sequences is indicated by a double line, and each sequence site in which a single base substitution has occurred in the W2939 strain is surrounded by a black frame.

FIG. 13 shows editing patterns in the sequences surrounding Target1 in the wild strain (WT) and T0-mutated strains (43-1, 49-1, #10-1, #25-1, #37-1, and #42-1), and base sequences of the respective strains. The sequence indicated in bold refers to a target sequence designed at the 5' side (Target1), the "TGG" sequence refers to the PAM sequence, and the "T" sequence at position 23 refers to a mutation site by the CRISPR/Cas9 system. Chimeras (49-3 and #9-4) indicate that transformed cells with different mutation patterns are considered to co-exist based on the waveform by Sanger sequencing.

FIG. 14 shows changes in amino acid sequences of T0-mutated strains. There are shown amino acid sequences around the target sequence (Target1) in the wild strain (WT), the W2939 strain, and the strains in which mutations are homozygously introduced. 'Mutation' indicates the type of mutation, and 'Polypeptide length' indicates the total length of polypeptide chains caused by translation (where, each symbol "a.a." indicates amino acid). Amino acid residues enclosed in a black frame indicate locations where mutations occurred. Each symbol "*" indicates stop codon.

DESCRIPTION OF EMBODIMENTS

Hereinafter, the present invention will be described in more detail.
1. Causative Gene Having Parthenocarpy and Mutation Thereof In an embodiment of the present invention, the causative gene expressing a parthenocarpic phenotype, i.e., characteristics of the fruit-bearing plant, is a Solyc10g038170 gene or ortholog thereof.

Figure 7:
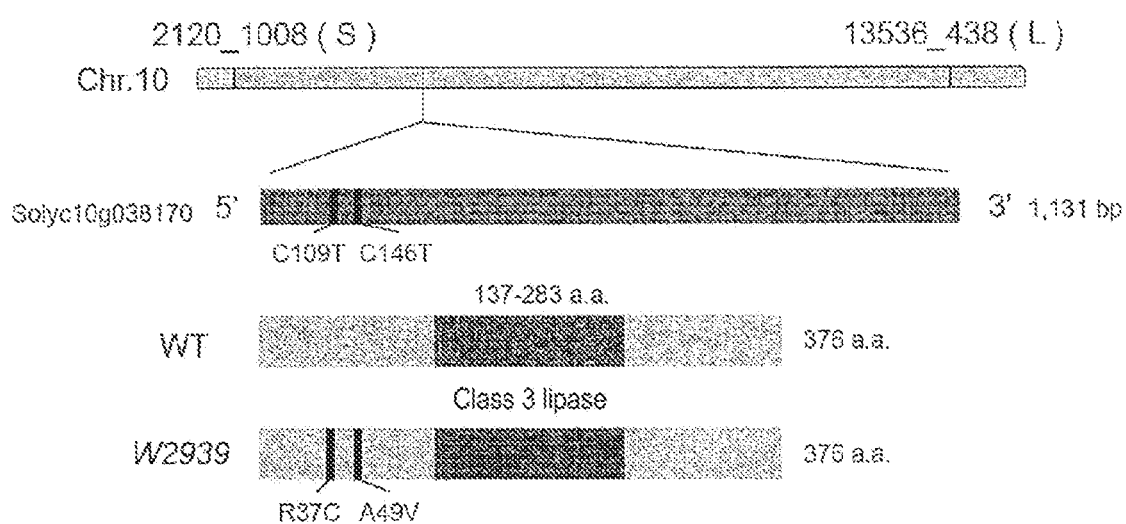
FIG. 7 shows a gene structure of Solyc10g038170 candidate causative gene for the W2939 parthenocarpic strain. 2120_1008 (S) denotes a short arm marker used in the snap-based cloning, and 13536_438 (L) denotes a long arm marker. The Solyc10g038170 is a gene with a total length of 1131 by and consists of only one exon, and the gene has a domain conserved in a class 3 lipase (triglyceride lipase). In the W2939 parthenocarpic strain, a single base substitution (C→T in each case) is inserted into each base at position 109 and position 146 from the 5' end, resulting in two amino acid missense mutations (R37C and A49V).

The above-described gene is present on chromosome 10 of the tomato plant (which may also be referred to as "crop"), and is presumed to be one of dad1 gene families. DAD1 protein is chloroplast phospholipase A1 that catalyzes the initial step of jasmonic acid biosynthesis. The Solyc10g038170 gene may be referred to as "S1dad1 gene", and includes a domain encoding a class 3 lipase (triglyceride lipase) activity (FIG. 7).

The Solyc10g038170 gene or ortholog thereof is a polynucleotide that may include, for example, a nucleotide sequence of SEQ ID NO: 1, or a nucleotide sequence having about 50% or greater, about 60% or greater, about 70% or greater, about 80% or greater, about 85% or greater, about 90% or greater, about 95% or greater, about 96% or greater, about 97% or greater, about 98% or greater, or about 99% or greater sequence identity to the nucleotide sequence. Alternatively, the above-described ortholog may have less than 50% sequence identity to the nucleotide sequence of SEQ ID NO: 1.

Further, the amino acid sequence of the protein encoded by the Solyc10g038170 gene or ortholog thereof may include an amino acid sequence of SEQ ID NO: 2, or a nucleotide sequence having about 50% or greater, about 60% or greater, about 70% or greater, about 80% or greater, about 85% or greater, about 90% or greater, about 95% or greater, about 96% or greater, about 97% or greater, about 98% or greater, or about 99% or greater sequence identity to the amino acid sequence. Alternatively, the above-described ortholog may have less than 50% sequence identity to the amino acid sequence of SEQ ID NO: 2.

Alternatively, when the nucleotide sequence of the Solyc10g038170 gene and ortholog thereof and the amino acid sequence encoded by the Solyc10g38170 gene and ortholog thereof are aligned, the region (or range) with the highest homology may have, for example, about 50% or greater, about 60% or greater, or about 70% or greater sequence identity. Examples of the region include regions at positions 52 to 240 of the nucleotide sequence of SEQ ID NO: 1 and regions at positions 18 to 80 of the amino acid sequence of SEQ ID NO: 2 (FIG. 9).

The term "ortholog" used herein refers to a group of homologous genes resulting from species branching from the common ancestral gene in the fruit-bearing plant, in which the genes are functionally homologous to each other in different biological species from tomato plants.

The "sequence identity (%)" used herein can be determined with or without an introduced gap between two sequences, preferably with an introduced gap, using a known protein or gene search system based on algorithm BLAST or FASTA (Zheng bhang et al., J. Comput. Biol., 2000; 7: 203-214; Altschul, S. F, et al., Journal of Molecular Biology, 1990; 215: 403-410; Pearson, W. R. et al., Proc. Natl., Acad. Sci. U.S.A., 1988; 85: 2444-2448).

The term "parthenocarpy" used herein refers to production of seedless fruits without pollination and fertilization in a plant, exhibiting enlargement of ovary, receptacles or the like without seed formation. In an embodiment of the present invention, the term "parthenocarpic" or "exhibiting parthenocarpy" refers to the property of a plant to cause parthenocarpy without the need for artificial parthenocarpic induction treatment such as plant hormone treatment or a certain physical stimulation.

As validated in the Examples below, the parthenocarpy relating to an embodiment of the present invention occurs when the mutation of the Solyc10g038170 gene or ortholog thereof includes a nucleotide sequence encoding an amino acid sequence including deletion, substitution, addition, or insertion of at least one amino acid in the amino acid sequence of the protein encoded by the gene or ortholog thereof, and the expression (or function) of the protein is reduced (or suppressed) or deleted by the mutation. In other words, the mutation described above includes whole or partial deletion, substitution, addition, or insertion of the nucleotide sequence of the Solyc10g038170 gene or ortholog thereof, which causes reduction or deficiency in the expression (or function) of the protein described above to the extent that parthenocarpy occurs, preferably causes disruption of the genetic function.

In this context, reduction or deficiency in the expression (or function) of the protein encoded by the Solyc10g038170 gene or ortholog thereof can be caused by deletion, substitution, addition, or insertion of at least one amino acid in the amino acid sequence of the protein. As in Examples to be described later, the parthenocarpy can be expressed by substitution of at least one amino acid in the amino acid sequence of the protein with at least one single base substitution as found in single nucleotide polymorphism (SNP). Examples of such single base substitution may include, but are not limited to, substitution of arginine at position 37 with another amino acid, substitution of alanine at position 49 with another amino acid in the amino acid sequence of SEQ ID NO: 2, and both the substitutions.

In the case of arginine at position 37, another amino acid described above is an amino acid other than arginine such as a hydrophilic amino acid (excluding arginine) or hydrophobic amino acid, for example, cysteine. In the case of alanine at position 49, another amino acid described above is an amino acid other than alanine such as a hydrophilic or hydrophobic amino acid (excluding alanine), for example, valine.

As examples of nucleic acid mutants, examples of polynucleotides including parthenocarpic gene mutation in the Solyc10g038170 gene or ortholog thereof include the nucleotide sequence of SEQ ID NO: 3. The sequence is the same as the sequence including single nucleotide polymorphisms of C109T and C146T at position 109 and position 146, respectively, in the nucleotide sequence of SEQ ID NO: 1 (where C is cytosine and T is thymine).

However, the mutation is not necessarily limited to the specific mutations described above, and parthenocarpy can be achieved as long as the genetic function of the mutation is reduced or disrupted.

Alternatively, gene modifying techniques such as genome editing and homologous recombination may be utilized to significantly or remarkably reduce (or decrease) or delete the expression of the gene or ortholog thereof by partial or full knock-out and disruption of the gene or ortholog thereof. Alternatively, the gene modifying techniques may be utilized to significantly or remarkably reduce (or decrease) the expression of the gene or ortholog thereof by insertion or addition of a different base sequence into the nucleotide sequence of the gene or ortholog thereof.

The structural form of the above-described mutations is not limited to the examples described above, and may be any structural form as long as it is possible to express parthenocarpy in a fruit-bearing plant.

Examples of orthologs of the Solyc10g038170 gene include, but are not limited to, orthologs described in Table 1 below.

TABLE 1

Examples of orthologs

| Plant name | Scientific name | Accession No. | SEQ ID NO: (amino acid sequence) |
|---|---|---|---|
| Potato | Solanum tuberosum | M1CJ51 | 88 |
| Aji amarillo | Capsicum baccatum | A0A2G2VSJ4 | 89 |
| Castor bean | Ricinus communis | B9RCZ2 | 90 |
| Robusta coffee | Coffea canephora | A0A068ULL0 | 91 |
| Eggplant | Solanum melongena | Sme2.5_02407.1_g00005.1 | 92 |
| Melon | Cucumis melo | MELO3C005944.2.1 | 93 |
| Courgette | Cucurbita pepo | Cp4.1LG17g10610 | 94 |
| Cucumber | Cucumis sativus | CSPI03G07100.1 | 95 |
| Grape | Vitis vinifera | XP_002270992.2 | 96 |

2. Parthenocarpic Plant

The fruit-bearing plant exhibiting parthenocarpy according to an embodiment of the present invention includes a mutation of a Solyc10g038170 gene or ortholog thereof, and the mutation causes reduction or deficiency in expression of a protein encoded by the Solyc10g038170 gene or ortholog thereof.

The Solyc10g038170 gene or ortholog thereof i.e., a causative gene having parthenocarpy, a mutation of the causative gene, and the above-described protein are as described in 1. above, and can be herein cited as they are.

In an embodiment of the present specification, plants nosed in genetic modification or transformation to impart parthenocarpy are fruit-bearing plants (e.g., plants including fruit vegetables and fruit trees), and examples thereof include cultivated plants whose fruits are edible. Examples of such plants include, but are not limited to, plants belonging to Solanaceae such as tomato (*Solanum lycopersicum*); eggplant (*Solanum melongena*), bell pepper (*Capsicum annuum* var. *grossum*), paprika (*Capsicum annuum*), shishito pepper (*Capsicum annuum* var. *grossum*), and potato (*Solanum tuberosum*); Cucurbitaceae such as cucumber (*Cucumis sativus* L.), melon (*Cucumis melo* L.), watermelon (*Citrullus lanatus*), squash (*Cucurbita*), and courgette (*Cucurbita pepo*), and oriental melon (*Cucumis melo* var. *makuwa*); Rosaceae such as strawberry (*Fragaria ananassa*) and apple (*Malas pumila*); Vitaceae such as grape (*Vitis* spp.); aji amarillo (yellow hot pepper; *Capsicum baccatum*, castor bean (*Ricinus; Ricinus communis*), and robusta coffee (*Coffea canephora*).

The plants described above are plants having no parthenocarpy, or having very low levels of parthenocarpy in the natural environment, and preferred plants are tomatoes (tomato plants).

Examples of tomatoes include, but are not limited to, tomato strains/varieties or derivatives thereof belonging to *Solanum lycopersicum, Solanum cerasiforme* (also referred to as "*Lycopersicon cerasiforme*"), *Solanum pimpinellifolium* (also referred to as "*Lycopersicon pimpinellifolium*", *Solanum cheesmanii* (also referred to as "*Lycopersicon cheesmanii*"), *Solanum parviflorum* (also referred to as "*Lycopersicon parviflorum*"), *Solanum chniielewskii* (also referred to as "*Lycopersicon chmielewskii*"), *Solanum hirsutum* (also referred to as "*Lycopersicon hirsutum*"), *Solanum pennellii* (also referred to as "*Solanum Lycopersicon pennellii*"), *Solanum peruvianum* (also referred to as "*Lycopersicon peruvianum*"), *Solanum chilense* (also referred to as "*Lycopersicon chilense*"), *Solanum lycopersicoides, Solanum habrochaites*, and the like.

As one example of tomato, the wild type tomato variety Micro-Tom (*Solanum lycopersicum* cv. Micro-Tom) (Scott J W, Harbaugh B K (1989) Micro-Tom A miniature dwarf tomato, Florida Agr. Expt, Sta. Circ. 370, pp, 1-6) is commercially available, and it is also available from the Tomato Genetics Resource Center (TGRC) (U.S.A.) under Accession No. LA3911. The wild type tomato variety Micro-Tom is a dwarf plant (approximately 10 to 20 cm in length) with small leaves and fruits, and it can also be crossed with a known tomato variety. The whole-genome sequence has been determined for the wild type tomato variety Micro-Tom (Kobayashi M, et al., Plant Cell Physiol. 2014; 55(2): 445-454).

The term "derivative" used herein refers to a progeny plant obtained by crossing a parent plant with a different plant strain/variety at least one time or through mutagenesis or mutation introduction in a parent plant.

The fruit-bearing plant of an embodiment of the present invention is a plant that can be obtained by modifying a gene of interest in the wild type plant exemplified above to cause reduction or deficiency in the expression (or function) of a protein encoded by the Solyc10g038170 gene or ortholog thereof, preferably to cause disruption the genetic function.

The genetic mutation includes whole or partial deletion, substitution, addition, or insertion of the nucleotide sequence of the Solyc10g038170 gene or ortholog thereof, the mutation causing reduction or deficiency in the expression (or function) of the protein described above to the extent that parthenocarpy occurs, preferably causing disruption of the genetic function. Modified examples include disruption by whole or partial knock-out of the gene or ortholog thereof, and introduction of a mutation in which arginine at position 37 is replaced with cysteine (R37C) and alanine at position 49 is replaced with valine (A49V), for example, in an amino acid sequence of SEQ ID NO: 2 of a protein encoding the gene. These mutations induce parthenocarpy. However, the mutation is not necessarily limited to the specific mutations described above, and parthenocarpy can be achieved as long as the genetic function of the mutation is reduced or disrupted.

The fruit-bearing plant of an embodiment of the present invention has characteristics in which a high parthenocarpic rate, a high fructification rate, and a high yield at a high temperature (e.g., an ambient temperature of 30° C. or higher) are imparted as compared with the wild type (not including the above-described mutation of the gene).

In this context, the parthenocarpic rate in the plant of an embodiment of the present invention is, for example, but is not limited to, 70% or greater, 75% or greater, 80% or greater, 85% or greater, 90% or greater, 95% or greater, 96% or greater, 97% or greater, 98% or greater, or 99% or greater. In Examples to be described later, the wild strain had a parthenocarpic rate of 57.1%, whereas the plant of an embodiment of the present invention (e.g., a tomato plant) had a high parthenocarpic rate of 99.4%. Furthermore, regarding the yields of plants, the wild strain and the plant of an embodiment of the present invention were compared based on the total weight of red-ripened mature fruits, the wild strain had a yield of 26.3±2.7 g, whereas the plant of an embodiment of the present invention (e.g., a tomato plant) had a yield of 63.1±2.5 g, which was about 2.4 times higher than that of the wild strain.

The fruit-bearing plant of the present invention is preferably homozygous (also referred to simply as "homo") for the above-described mutation of the Solyc10g038170 gene or ortholog thereof. Since the fruit-bearing plant is a homo-plant, two alleles have the same mutation. In contrast, when the fruit-bearing plant is heterozygous (also referred to simply as "hetero"), one of the two alleles is normal and the other is a mutant.

Due to the mutation of the Solyc10g038170 gene or ortholog thereof, the plant of an embodiment of the present invention may have a phenotype such as early enlargement of ovary, protrusion of styles, discoloration of anther tube tip, or remained petals or styles after the ovary enlargement (see Examples to be described later).

The present invention further provides a portion of the plant, in addition to a plant body of the fruit-bearing plant.

The portion of the plant includes, but are not limited to, stems, leaves, roots, flowers, buds, fruits, seeds, tissues, cells, callus, and the like. Here, callus is an artificial mass of cells formed when a portion of a plant body is cultured in a culture medium containing a plant hormone (e.g., auxin, cytokinin, etc.). The portion of the plant as described above includes a mutation of a Solyc10g038170 gene or ortholog thereof, the mutation causing reduction or deficiency in expression of a protein encoded by the Solyc10g038170 gene or ortholog thereof.

3. Method for Producing Parthenocarpic Fruit-Bearing Plant

The present invention further provides a method for producing the fruit-bearing plant described in 2. above, the method including:

(1) introducing a mutation of a Solyc10g038170 gene or ortholog thereof into a cell, callus or tissue (including a portion of a plant) of a wild type of the plant, the mutation causing reduction or deficiency in expression of the Solyc10g038170 gene or ortholog thereof;

(2) culturing the cell, callus or tissue of the plant (transformant) in the step (1) to form a plant body population; and (3) selecting a plant having parthenocarpy from the plant body population in the step (2).

Hereinafter, the steps (1) to (3) will be described.

<3.1> Step (1)

This step introduces the mutation of the Solyc10g038170 gene or ortholog thereof in the cells, callus or tissues (including parts of a plant) of a wild type plant.

This genetic mutation includes reduction or deficiency in the expression of the above-described gene or ortholog thereof so that, for example, the disruption or deficiency of the gene is achieved by knock-out of the gene using a gene modifying technique such as a genome editing technique or a homologous recombination technique.

An example of the mutation is a disruption or deficiency in the Solyc0g038170 gene or ortholog thereof.

Another example of the mutation is to introduce a polynucleotide including a mutation caused by a single base substitution, for example, in a nucleotide sequence of SEQ ID NO: 1 of the Solyc10g038170 gene or a nucleotide sequence of ortholog of the gene, at a position or positions corresponding to position 109, position 146, or both position 109 and position 146 in a nucleotide sequence of SEQ ID NO: 1, or at a position in a nucleotide sequence of the ortholog corresponding to the position or positions. An example of the polynucleotide is a polynucleotide including the nucleotide sequence of SEQ ID NO: 3.

Genome editing is a technique for editing and genetically modifying genomic DNA using an artificial cleavage enzyme, e.g., TALEN (TALE nuclease), a CRISPR-Cas system, and the like. Any genome editing technique can be used in the method of the present invention, and the CRISPR-Cas system is preferably used.

In particular, the CRISPER-Cas9 system has been discovered from an adaptive immune system for viruses and plasmids of bacteria and archaea, and the system allows for relatively simple construction of vectors and simultaneous modification of multiple genes (Jinek et al., Science, 17,337 (6096): 816-821, 2012; Sander et al., Nature biotechnology, 32 (4): 347-355, 2014). The system includes a Cas9 protein and single guide RNA (sgRNA) having a target sequence with about 20 base pairs. Coexpression of the Cas9 protein and the sgRNA in a plant body causes the sgRNA to recognize a PAM sequence near the target sequence and specifically binds to the target genomic DNA, and the Cas9 protein induces double-strand break (DSB) at the upstream of the PAM sequence. Currently, widely used Cas9 protein is a SpCas9 type, and there is less restriction on the position of mutation introduction since the PAM sequence is NGG. The CRISPR/Cas9 system has been already utilized as a mutagenesis technique for plants, and has been confirmed to be applicable for the first time in tomatoes in 2014 (Brooks et al., Plant physiology, 166 (3): 1292-1297, 2014).

The target gene in the present invention is a Solyc10g038170 gene or ortholog thereof. The sequence of the Solyc10g038170 gene or ortholog thereof is, for example, a polynucleotide sequence of SEQ ID NO: 1, or a nucleotide sequence having about 50% or greater, about 60% or greater, about 70% or greater, about 80% or greater, about 85% or greater, about 90% or greater, about 95% or greater, about 96% or greater, about 97% or greater, about 98% or greater, or about 99% or greater sequence identity to the polynucleotide sequence.

In the nucleotide sequence of the gene or ortholog thereof, for example, as can be recognized by Cas9, a region with the PAM sequence can be selected as a target sequence. In this case, the PAM sequence is, for example, NGG (where N is any base). Examples of the target sequence in the nucleotide sequence of SEQ ID NO: 1 include the sequences described below. Three bases (underlined) at the 3' end of these sequences are NGG.

```
                                     (SEQ ID NO: 79)
   G T A T G T T T A A T G T T A G G G A G A G G (SEQ ID NO: 80)
   A C A T A C C A T A T G T T G C C C C A T G G (SEQ ID NO: 81)
   G C T T G T G G A A G A T A G T C A A T G G G (SEQ ID NO: 82)
   G G A C A G A G C C C A G A G A A A A T A G G (SEQ ID NO: 83)
   A T A T T A A T C C C A T T A A A G T G T G G (SEQ ID NO: 84)
   G T A A C A G T C A T G T C C T T T G G T G G (SEQ ID NO: 85)
   G G G T T G A T A A A G C T C C T A A A T G G (SEQ ID NO: 86)
   T G T T G C C C G A T G G T T G A A A G T G G (SEQ ID NO: 87)
   C C A C T A G A T G A T A A T T T A C G T G G
```

Examples of Cas9 include SpCas9 derived from *S. pyogenes*, SaCas9 derived from *S. aureus*, and StCas9 derived from *S. thermophiles*. The PAM sequence varies depending on the origin of Cas9. For example, the SpCas9 recognizes NGG (N is any base).

The snRNA is a polynucleotide including nucleotide sequences complementary to nucleotide sequences of preferably 18 to 26 bases, for example, 20 to 24 bases, from one base upstream of the PAM sequence in the target gene.

Examples of promoters include a ubiquitin promoter, a U6 promoter, a CaMV35S promoter, and other plant tissue-specific promoters.

Figure 10:
FIG. 10 shows the vector construct for genome editing and a model for production of Cas9 vector, where Cas9 denotes a sequence encoding a Cas9 protein derived from *Streptococcus pyogenes*, pUbi denotes a Petroselinum crispum ubiquitin promoter, tPea3A denotes a Glycine max 3A terminator, pU6 denotes an Arabidopsis thaliana. U6 promoter, sgRNA denotes single guide RNA, pNOS denotes a promoter from Nopaline Synthase gene, NPTII denotes a kanamycin-resistance gene, tNOS denotes a terminator from Nopaline Synthase gene, RB denotes T-DNA boundary sequence from *Agrobacterium* (Right-border), and LB denotes T-DNA boundary sequence from *Agrobacterium* (Left-border).

Examples of expression vectors include a vector containing a nucleotide sequence encoding the Cas9 described above, an sgRNA sequence, a promoter sequence, a drug resistance gene or a reporter gene, and a terminator; and a binary vector containing a T-DNA boundary sequence derived from *Agrobacterium* (Right-border), and a T-DNA boundary sequence derived from *Agrobacterium* (Left-border), in addition to the above elements. Examples of vectors include pUC-based, pBluescript-based, pBI-based, and pPZT-based vectors. One example of a binary vector is shown in FIG. 10 (an example when two targets are included).

Each of the vectors described above can be introduced into a plant body, cell, callus, tissue (including parts of a plant, such as leaves, roots, and stems) by, for example, the *Agrobacterium* method, electroporation method, or protoplast method.

Figure 11:
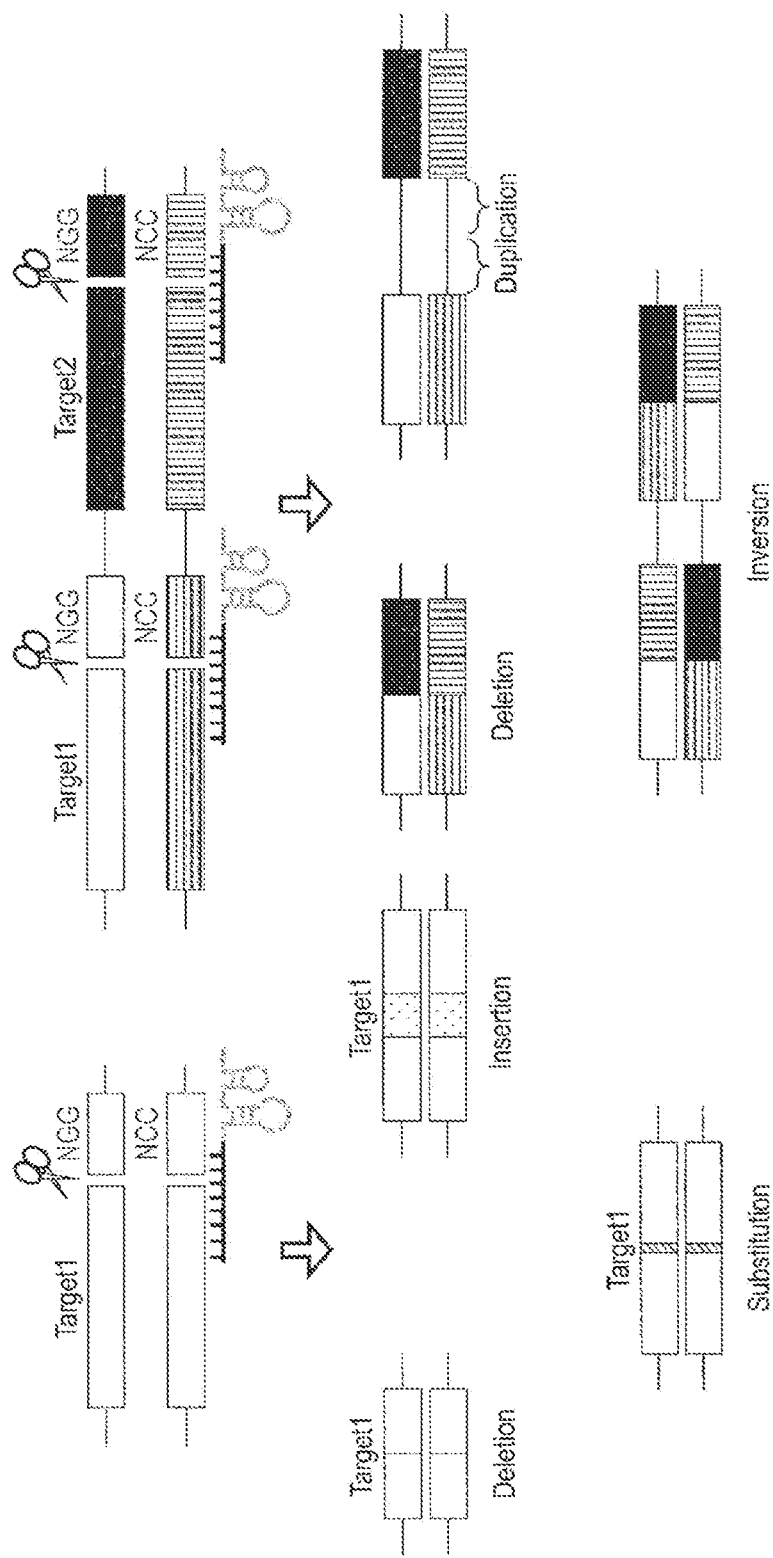
FIG. 11 shows mutagenesis models by a Crispr/Cas9 system. In the case of a target sequence at one position, insertion, substitution, and deletion initiations are caused by non-homologous end-joining (NHEJ) repair. In the case of target sequences at two positions, large-scale deletion, inversion, and duplication mutations may occur.

Utilization of genome editing allows a mutation of the target gene of an embodiment of the present invention to be introduced by cleavage, deletion or (partial or complete) disruption (knock-out), exogenous gene insertion (knock-in), substitution, duplication, inversion, or the like (FIG. 11). Exogenous gene insertion and specific base substitution are achieved by inserting an exogenous gene sequence and a sequence containing a specific base to be substituted into each of the vector in advance so that these sequences can be expressed. The exogenous gene sequence is, for example, a nucleotide sequence of SEQ ID NO: 3. The above-described mutations result in imparting at least parthenocarpic phenotype, further high fructification rate, high temperature resistance, high yield, and the like to plants.

<3.2> Step (2)

In this step, the cells (including cultured cells (mass of cells) of the plant (transformant), callus or tissues (including parts of the plant) in the step (1) are cultured to form a plant body population.

Culture can be performed by tissue culture (usually at 20 to 30° C.) using a solid medium or a liquid medium. The culture medium is a medium as used in plant tissue culture, and examples thereof include culture media (usually, a pH of 5.5 to 6) containing yeast extract, coconut milk, amino acids, saccharides (e.g., sucrose), growth regulators (e.g., 2,4-D (2,4-dichlorophenoxy acetic acid), NAA (α-naphtalenacetic acid), IAA (indole-3 acetic acid)), vitamins (e.g., thiamine, calcium pantothenate, biotin, folic acid, nicotinic acid), and inorganic salts.

<3.3> Step (3)

In this step, a plant having parthenocarpy is selected from the plant body population in the step (2).

The above-described selection includes detecting reduction or deficiency in expression of a Solyc10g038170 gene or ortholog thereof in a cell or tissue isolated from the produced plant body population, or a disruption or deficiency in the gene or ortholog thereof. The detection method can include a PCR method, a hybridization method, and the like as described in 3.4 below.

For example, the use of the FISH method makes it possible to confirm that the above-described mutation of the Solyc10g038170 gene or ortholog thereof is present in both the two alleles and the selected plant is homozygous for the mutation.

The selected parthenocarpic plants can be cultivated using a cultivation method suitable for plants. Cultivation can be carried out by any cultivation method such as hydroponic cultivation, facility cultivation (e.g., greenhouse cultivation or plant factory cultivation), open-field cultivation, or planter cultivation.

4. Method for Selecting Parthenocarpic Plant

The present invention further provides a method for selecting a parthenocarpic plant from fruit-bearing plants, the method including detecting suppression in expression of a Solyc10g038170 gene or ortholog thereof in a cell or tissue of the fruit-bearing plant, or a disruption or deficiency in the gene or ortholog thereof.

The method includes: isolating genomic DNA (chromosome) or total RNA from cells or tissues of a plant; synthesizing cDNA from the RNA as necessary; and then bringing primers or probes (including labels such as fluorescent dyes as necessary) prepared in advance into contact with the DNA or RNA or cDNA, the primers or probes being specific to the Solyc10g038170 gene or ortholog thereof, and performing hybridization (including the FISH method and SNP analysis method) or polymerase chain reaction (PCR; including quantitative RT-PCR).

As necessary, the presence or absence of a protein encoded by the Solyc10g038170 gene or ortholog thereof in the cell may be examined by, for example, immunoassay, or alternatively, the presence or absence of a mutation in the protein may be examined by sequencing.

EXAMPLES

The present invention will be more specifically described with reference to the following examples. However, these examples are not intended to limit the scope of the present invention.

Example 1

<Production and Characteristics of Parthenocarpic Tomato W2939 Strain>

1. Plants Under Test and Cultivation

A W2939 (TOMJPV2939) strain exhibiting parthenocarpy was selected from a lame-scale tomato mutant population obtained by treating Micro-Tom i.e., the dwarf model variety of tomato (*Solanum lycopersicum* L.) with ethyl methanesulfonate (EMS). $BC_2S_2$ and $BC_3S_2$ strains obtained by backcrossing the wild strain "Micro-Tom" into the W2939 strain, and an $F_3$ hybrid strain crossed with a grape tomato variety "Ueleie106WP" were used in the following experiments.

Cultivation was carried out in the (14 greenhouse in the Tsukuba-Plant Innovation Research Center (Tsukuba City, Ibaraki, Japan), and in the closed cultivation room in the 2D building at the University of Tsukuba. The $BC_2S_2$ strain and the $F_3$ hybrid strain were cultivated in the 64 greenhouse in the summer (from May to October). Seeds germinated in a petri dish were transferred to Jiffy pots (Sakata, seeds) tilled with Jiffy mix (Sakata seeds). A nutrient film technique (NFT) system was used for water supply in the greenhouse. A nutrient solution prepared by using OAT House A formulation (1.5 g/L, OAT House 1; 1 g/L, OAT House 2, OAT Agrio Co., Ltd.) at an electric conductivity (EC) of 1.2 to 1.3 dS/m was circulated for 15 minutes every 3 hours between 6:00 and 18:00. After a high-temperature period, that is, a period starting from July, the EC was increased to about 1.8 in order to prevent nutrient shortage. During the cultivation period, a fan was operated in the greenhouse, skylight and side windows were opened, and direct sunlight was shielded by a blackout curtain to maintain a temperature at which a plant body can grow. The light period during cultivation was from 12 to 13.5 hours.

Further, the $BC_3S_2$ strain was cultivated in the closed cultivation room in the summer (from May to September). The seeds germinated in the petri dish were transferred to a rockwool cube (Grodan) and cultivated using an NFT system similarly to the greenhouse. As a nutrient solution, OAT House A formulation (OAT Agrio Co., Ltd.) was used, and EC was adjusted to 1.5. Irrigation was set to be performed every morning at 8 am for 15 minutes. The room temperature was kept constant at 24° C., and the light period was set at 16 hours. In each of the strains, the plant body was covered with a wrap for two days after the transfer, and a space was gradually provided for acclimation.

2. Study of Parthenocarpic Rate

The parthenocarpy of the $BC_2S_2$ obtained by backcrossing the W2939 strain with the "Micro-Tom" wild strain under high temperature conditions was evaluated by an emasculation method. 5 individuals of the $BC_2S_2$ parthenocarpic strain and 4 individuals of the wild strain were tested, and 10 to 20 flowers per individual were emasculated 2 days before flowering. As a comparison in a case where environmental conditions were changed, the $BC_3S_2$ strain obtained by backcrossing the "Micro-Tom" wild strain into the W2939 strain, which was cultivated in the closed cultivation room, was also evaluated. 4 individuals of the $BC_3S_2$ parthenocarpic strain, 4 individuals of the $BC_3S_2$ non-parthenocarpic strain, and 3 individuals of the wild strain were tested, and 10 to 15 flowers per individual were emasculated 2 days before flowering. Vibration pollination was performed on the first flower truss so as not to cause any adverse effect on the fructification rate due to the non-fertilization of the first flower truss. Determination was carried out about 10 days after flowering, and the fruit having a diameter of 5 mm or greater was determined as parthenocarpic fruit.

The parthenocarpy of $F_3$ hybrid strain obtained by crossing W2939 strain with "Ueleie106WP" wild strain was determined by the emasculation method. Each bud after the third flower truss was emasculated 2 days before flowering so as not to cause fructification via fertilization. Vibration pollination was performed on the first flower truss so as not to cause any adverse effect on the fructification rate due to the non-fertilization of the first flower truss. Determination was carried out about 10 days after flowering, and the fruit having a diameter of 1 mm or greater was determined as parthenocarpic fruit.

3. Study of Yield

The $BC_2S_2$ strain was used to validate the difference in fruit yield with the wild strain under high temperature stress conditions. The seeds were seeded in May and transferred to the greenhouse after germination. The total weights of red ripe fruits harvested in the period from August to early October were compared between strains. Individuals which had not been used in the study of parthenocarpy were tested in the study of yield.

Furthermore, the yield study was performed using the $F_3$ hybrid strain. Regarding one representative individual of the $F_3$ hybrid parthenocarpic strain, $F_3$ hybrid non-parthenocarpic strain, and "Ueleie106WP" wild strain seeded in May, red ripe fruits and green ripe fruits were collected in early September. Only the green ripe fruits having a diameter of 1 cm or greater were collected. No quantitative study was performed, because the individuals for the study of yield overlapped with those for the study of parthenocarpic rate.

4. Results 4. 1 Parthenocarpy of W2939 Strain

In order to examine the strength of parthenocarpy due to the genetic mutation occurred in the W2939 strain, the parthenocarpy of $BC_2S_2$ and $BC_3S_2$ strains obtained by crossing the W2939 strain and the "Micro-Tom" wild strain was evaluated by the emasculation method. First, evaluation under high temperature conditions was conducted in the summer (August to October). As plant bodies, 5 individuals of the $BC_2S_2$ parthenocarpic strain, 4 individuals of the "Micro-Tom" wild strain were tested. 11 to 14 flowers per individual were emasculated in the case of the parthenocarpic strain, and 18 to 20 flowers per individual were emasculated in the case of the wild strain. The average temperature from the blossoming of the first flower truss in late June to the start of emasculation in early August was 30° C. or higher in many days, and the highest temperature exceeded 40° C. in some days. Under such environmental conditions where the fructification via fertilization was severe, the presence or absence of enlargement of emasculated ovary was determined, and 19% (12 out of 63 flowers) of the parthenocarpic strain and 4% (3 out of 77 flowers) of the wild strain fructified (FIG. 1). As an additional experiment, the parthenocarpic rate in the case of cultivating the W2939 strain (mutant) at a growth appropriate temperature of 24° C. was examined. As plant bodies, 4 individuals of the $BC_3S_2$ parthenocarpic strain, 4 individuals of the non-parthenocarpic strain, and 3 individuals of the "Micro-Tom" wild strain were tested, and 3 to 15 flower per individual were emasculated. As a result, all the wild strains did not fructify, but 9.8% (4 out of 41 flower) of the $BC_3S_2$ parthenocarpic strain and 8.5% (5 out of 59 flower) of the $BC_3S_2$ non-parthenocarpic strain fructified.

In order to evaluate the parthenocarpy in the case of crossing with another variety, the same evaluation test was performed using the $F_3$ strain obtained by crossing the W2939 strain and the "Ueleie106WP" wild strain. Cultivation was carried out in the summer (from May to September) in order to evaluate the strength of parthenocarpy under high temperature stress. The average temperature in this period was 25° C. or higher. In the second half of the growth period, the temperature was 30° C. or higher almost every day. The highest temperature often reached 35° C. in the first half of the growth period, and reached 40° C. or higher from late June, which was a severe high temperature condition for fructification, just as last year. The "Ueleie106WP" wild strain and the $F_3$ strain were grown in this cultivation environment, flowers were emasculated 2 days before flowering in June and July, and the parthenocarpy was examined. In the $F_2$ hybrid population, a strain having a high fructification rate was determined to have heat tolerance, and a strain having a low fructification rate and showing no heat tolerance was determined to have no heat tolerance, and the next generation of each of the strains was used for the study. 4 individuals of each of the $F_3$ hybrid strain and the "Ueleie106WP" wild strain were tested, and 20 flowers per individual were emasculated. As a result of determining the presence or absence of enlargement of emasculated ovary; the "Ueleie106WP" wild strain had a parthenocarpic rate of 0%, and the $F_3$ hybrid strain showing no heat tolerance had a parthenocarpic rate of 13.8%. However, the strain showing heat tolerance had a parthenocarpic rate of 57.5%. This result suggests that when crossing with indeterminate variety "Ueleie106WP", the parthenocarpic rate can be improved as compared with the case where the genetic background is "Micro-Tom".

4.2 High Temperature Resistance of W2939 Strain

The yield of red ripe fruits was examined using 6 individuals of the parthenocarpic $BC_2S_2$ strain obtained by backcrossing with the "Micro-Tom" wild strain. The yield (average) of the "Micro-Tom" wild strain in August and September was 26.3±2.7 g. Meanwhile, the yield (average) of the parthenocarpic $BC_2S_2$ strain was 63.1±2.5 g, and the yield was increased by about 2.4 times (FIG. 2). This result shows that the parthenocarpy was highly likely to be linked with high temperature resistance (yield maintenance under high temperature stress). This emasculation was conducted while the petals were left. Thus, it was quite possible that these plant hormones were produced in the petals and acted on the ovary. In addition to the "Micro-Tom" background strain, also for the $F_3$ hybrid strain obtained by crossing the "Ueleie106WP" wild strain and the W2939 strain (mutant), red ripe fruits and green ripe fruits of 1 individual of each of the strains were collected 123 days after seeding, and the yields were compared. This result confirmed that the fructification rate was low in the progenies of the wild strain having no heat tolerance and the $F_2$ having no heat tolerance, but the fructification rate was improved in the progeny having high temperature resistance, thereby maintaining the yield. Therefore, it was suggested that imparting of the parthenocarpy resulted in maintaining of yield under high temperature stress.

4.3 Characteristics of Fruit Trait

Fruit traits such as fruit weight, seed rate, and sugar content (Brix value) are important traits that influence the taste of tomato. Regarding these traits, interstrain comparison was conducted using the "Micro-Tom" wild strain and the $BC_2S_2$ parthenocarpic strain cultivated in an outdoor greenhouse, and the "Micro-Tom" wild strain and the $BC_3S_2$ strain cultivated in a closed cultivation room.

Figure 3:
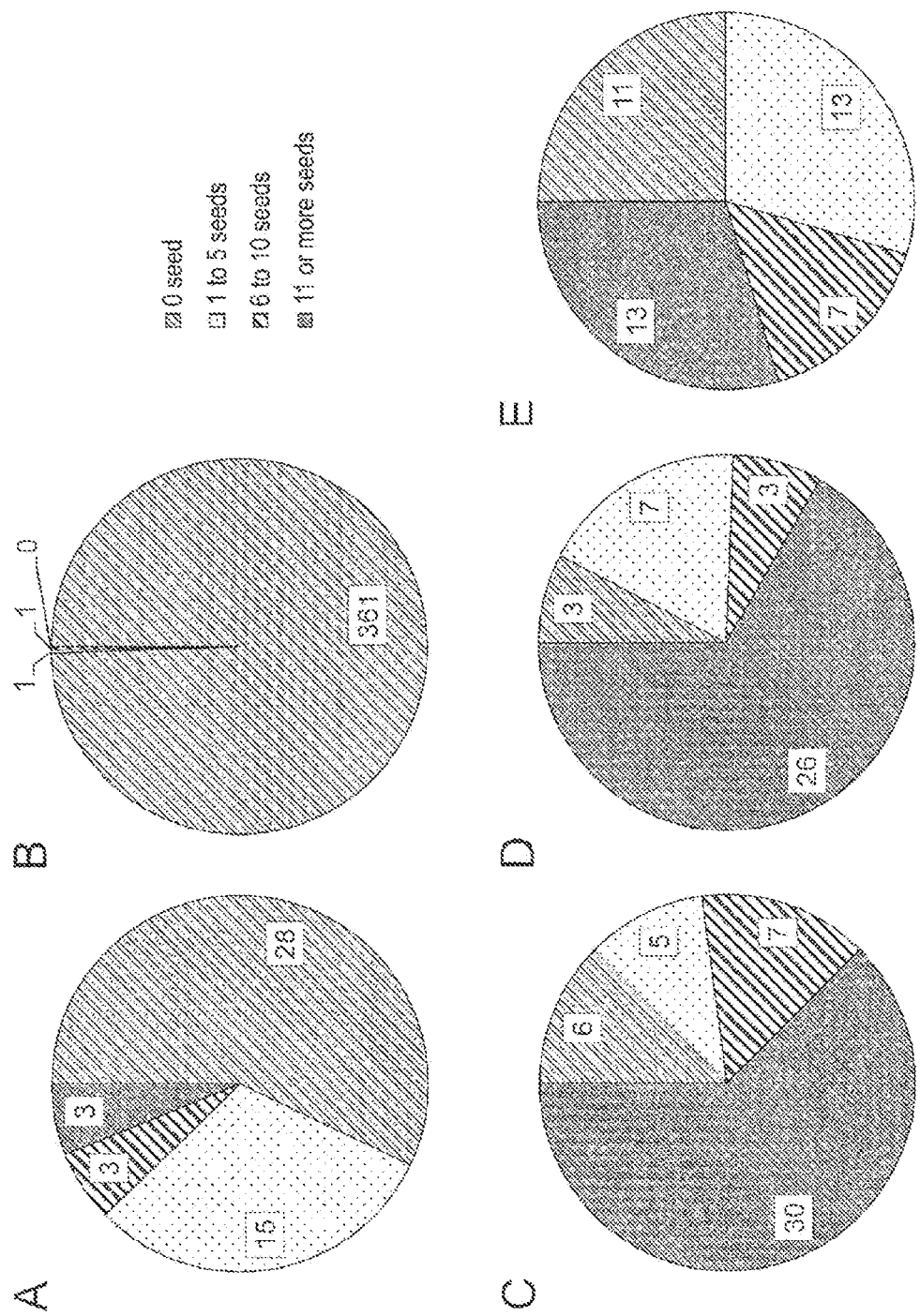
FIGS. 3A to 3E show the proportion of the tomato fruits with seeds and the number of seeds.

The average fruit weight in the "Micro-Tom" wild strain cultivated in the greenhouse was 3.28±0.23 g, whereas the average fruit weight in the $BC_2S_2$ strain was 1.74±0.06 g (p<0.01). The seed rate in the wild strain was 42.9% (21 out of 49) and the seed rate in the $BC_2S_2$, strain was 0.6% (2 out of 363). The average fruit weight in the "Micro-Tom" wild strain cultivated in the closed cultivation room was 3.33±0.26 g, whereas the average fruit weight in the $BC_3S_2$ non-parthenocarpic strain was 2.83±0.23 g, and the average fruit weight in the $BC_3S_2$ parthenocarpic strain was 2.73±0.19 g. A Tukey-Kramer test was conducted, and no significant difference was observed between the strains. The seed rate in the wild strain was 87.5% (42 out of 48), the seed rate in the $BC_3S_2$ non-parthenocarpic strain was 92% (36 out of 39), and the seed rate in the $BC_3S_2$ parthenocarpic strain was 75% (33 out of 44) (FIG. 3). These results reveal that the W2939 mutant parthenocarpic strain exhibits conditional parthenocarpy in which seeds could be produced by self-fertilization under the environmental conditions causing no pollen sterility. In the $BC_3S_2$ mutant, the number of seeds tended to decrease. As for the fruit weight, seedless fruits of the parthenocarpic strain had a small fruit weight, but a decrease in fruit weight was suppressed for the fruits with seeds (FIG. 3). The decrease in fruit weight in the seedless fruits has also been confirmed in the procera mutant, and the authors have pointed out the possibility that auxin which would otherwise be supplied was deficient due to the absence of seed formation, and cell division, particularly at the site of the pulp is suppressed (Carrera. et al., Plant physiology, 2012; 160 (3): 1581-96). Furthermore, an increase in the number of fructified plants associated with parthenocarpy was considered as another cause. As for the average number of red ripe fruits in a certain period measured in the study of yield described above, the average number was 8.0±0.9 in the "Micro-Tom" wild strain, but the average number was increased by 4 times or more to 36.3±3.1 in the $BC_2S_2$ parthenocarpic strain produced from the W2939 strain.

Figure 4:
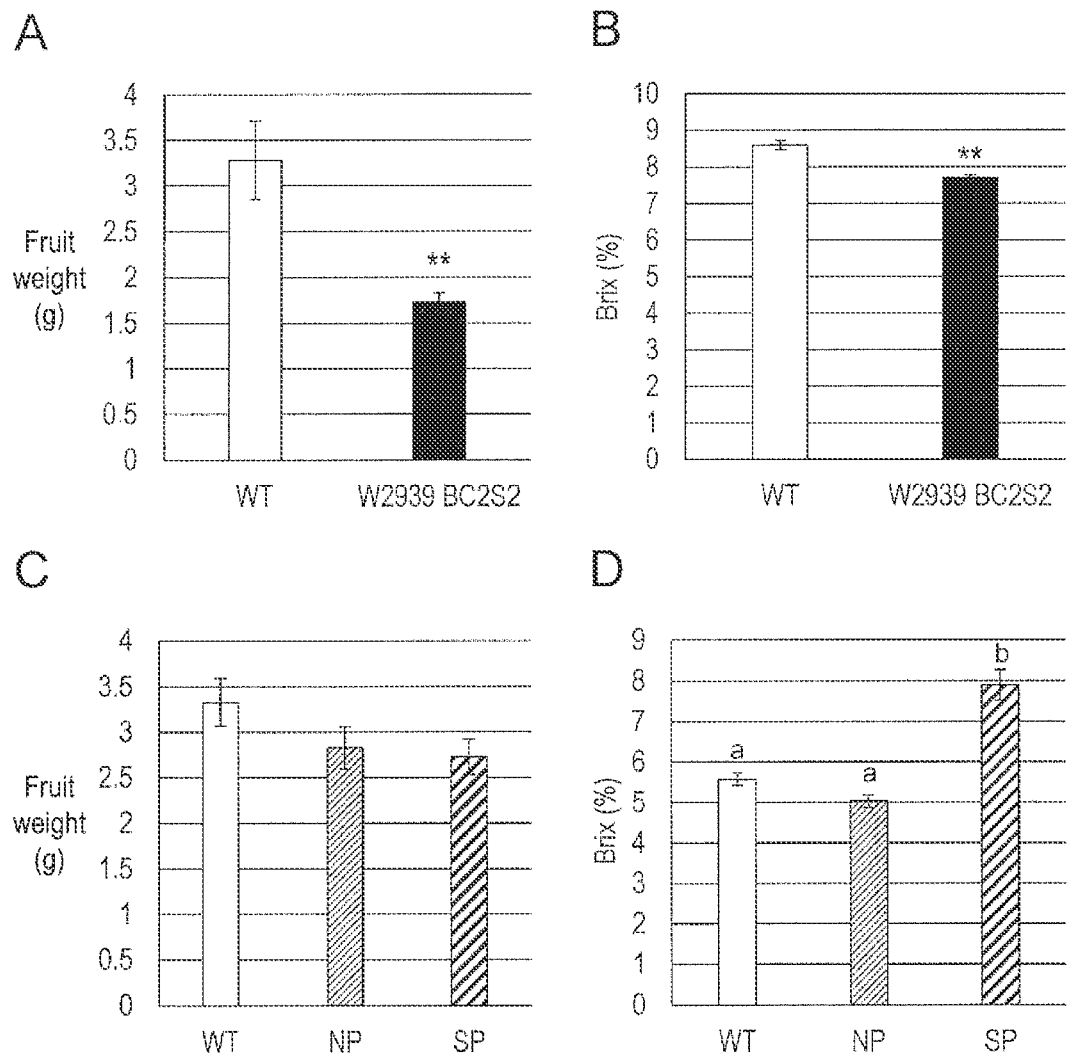
FIGS. 4A to 4D shows the fruit weights (weights) and the sugar contents (Brix values).

In this example, the Brix value was used as an indicator of sugar content. As a result of the measurement, the average Brix value in the "Micro-Tom" wild strain cultivated in the greenhouse was 8.59±0.12%, and the average Brix value in the $BC_2S_2$ strain was 7.70±0.06%, but no significant difference was found in the Student's t-test. Meanwhile, the average Brix value in the "Micro-Tom" wild strain cultivated in the closed cultivation room was 5.57±0.15%, whereas the average Brix value in the $BC_2S_2$ non-parthenocarpic strain was 5.02±0.15% and the average Brix value in the $BC_2S_2$ parthenocarpic strain was 7.90±0.37%. The Tukey-Kramer test was conducted, a 1% level of significant difference was found between the parthenocarpic strain and the non-parthenocarpic strain and between the parthenocarpic strain and the wild strain (FIG. 4). The above-described results revealed an increase in Brix value in fruits of the parthenocarpic strain of the W2939 strain.

Example 2

<Identification of Parthenocarpic Causative Gene and Mutation>

1. Narrowing of Gene Regions by Map-Based Cloning Method 1.1 Plants under Test and Cultivation Conditions $F_2$ seeds were obtained by crossing the W2939 (TOMJPW2939) strain and the wild strain of grape tomato variety "Regina" (Sakata seeds). This $F_2$ hybrid population was seeded in April and kept warm in an incubator in a (14 glass greenhouse for 5 days. Thereafter, the resultant population was transferred to a device for nutrient film technique in the greenhouse and cultivated, and only individuals clearly exhibiting parthenocarpy among all 314 individuals were tested. As fur the temperature conditions during the cultivation period, the temperature in the daytime was from 25 to 40° C. the temperature in the night-time was from 15 to 25° C., and the temperature in the light period was from 13 to 14.5 hours. Water supply was carried out by circulating a nutrient solution prepared by using OAT House A formulation (1.5 g/L, Otsuka 1; 1 g/L, Otsuka 2, OAT Agrio Co., Ltd.) at 1.2 to 1.3 dS/m for 5 minutes every 1 hour between 9:00 and 16:00.

1.2 Determination of Parthenocarpy Based on Flower Phenotype

The parthenocarpy was determined based on the flower phenotype at the flowering stage. An individual in which protrusion of styles or anther tube dehiscence due to early enlargement of ovary, and incomplete detachment of petals and styles were observed in floral organs was determined to be a parthenocarpic individual.

1.3 Extraction of Genomic DNA

Young leaves were sampled into 1.5 ml tubes and 400 µl of DNA extraction buffer was added. The DNA extraction buffer was prepared by adding distilled water to 4 ml of 200 mM Tris, 10 ml of 250 mM NaCl, 1 ml of 25 mM EDTA, and 1 ml of 0.5% SDS to make 20 ml.

The solution containing leaves ground with a pestle was centrifuged at 13,200 rpm for 2 minutes, and 300 µl of supernatant was added to new 1.5 ml tubes. Isopropyl alcohol was added in an equal amount of 300 µl to cause DNA to be precipitated. After shaking of the tubes for 2 minutes, centrifugation was performed at 13,200 rpm for 5 minutes. The tubes after centrifugation were carefully tilted to discard the solution, 1 ml of 70% ethanol was added, and the mixture was centrifuged at 13,200 rpm for 5 minutes. The solution was discarded, and the tubes were dried in air for about 30 minutes till sufficiently dried. Thereafter, 100 µl of 1×TE solution was added thereto, the tubes were shaken for 5 minutes and stored at 4° C. The concentration of samples after completion of extraction was measured using NanoDrop 2000 (Thermo Fisher Scientific).

1.4 Selection of SNP Marker for Rough Mapping

Kazusa DNA Research Institute (Kisarazu, Chiba, Japan) had developed 559 SNP markers showing polymorphism between "Micro-Tom" and "Regina", and made the SNP markers publicly available for searching on the Kazusa Tomato Genomics Database. Among the SNP markers, the markers located on the short arm and long arm of chromosomes 1 to 12 were selected, and SNP marker information and sequences of 50 base pairs before and after the SNP were obtained.

1.5 Primer Design

The sequence information acquired in 1.4 above was input into BLAST search of the Sol Genomics Database to acquire surrounding sequences of about 300 base pairs before and after the SNP. Primers were designed such that about 150 base pairs before and after the SNP could be amplified using a primer design tool: Primer 3.

1.6 PCR Reaction

The PCR reaction was conducted using the above-described DNA coarse extract and primers. An enzyme for PCR, KOD FX Neo (TOYOBO CO., LTD., Osaka, Japan), was used. The composition of the reaction solution was: 0.3 µl of KOD FX Neoo (1.0 U/µl), 7.5 µl of 2×Buffer, 3.0 µl of 2 mM dNTPs, 0.3 µl of Fw Primer (10 µl), 0.3 µl of Rv Primer (10 µl), 3.3 µl of distilled water, and 0.3 µl of template DNA (15 µl in total).

PCR conditions were: PCR at 94° C. for 2 minutes, followed by 35 repetition of one cycle including PCR at 98° C. for 10 seconds, 59° C. for 30 seconds, and 68° C. for 30 seconds. Thereafter, PCR was conducted at 68° C. for 7 minutes.

1.7 Electrophoresis

A 1% Star agarose gel (Rikaken) was used for electrophoresis of PCR products. 5 µl of the PCR reaction solution was mixed with 0.6 µl of 10×loading dye (Takara Bio Inc., Kyoto, Japan), the agarose gel was set in an electrophoresis tank filled with 1×TAE buffer, and the mixed liquid was applied. Electrophoresis was performed at 100 V for 15 minutes to confirm whether the surroundings of SNP site were specifically amplified. The used DNA marker was Gene Ladder Wide 1 (Wako). After electrophoresis, the presence or absence of a band was confirmed under UV in a gel documentation imaging system E-BOX-Vx2/20M (Vilber Lourmat).

1.8 Exostar Treatment

In order to remove unreacted primers and dNTPs, the PCR products were treated with ExoStar using Exonuclease I (New England Biolabs) and Shrimp Alkaline Phosphatase (rSAP, New England Biolabs). The solution composition included 1 µl of Exonuclease I, 1 µl of rSAP, 1 µl of distilled water (DW), and 5 µl of PCR product (8 µl in total). The reaction was carried out at 37° C. for 60 minutes and 80° C. for 15 minutes.

1.9 Direct Sequencing

The reaction solution treated with ExoStar was diluted 30 times with DW. The diluent was used to prepare a pre-mix solution for direct sequence. The composition of the pre-mix solution was: 1 µl of diluent (×30), 3 µl of Fw Primer (3.2 pmol/µl), and 17 µl of DW (21 µl in total). Value Read sequence service (Eurofins Genomics K.K.) was used for direct sequencing. From the analysis results, it was determined which genotype of "Micro-Tom" homo, hetero, or "Regina" homo each parthenocarpic individual had.

2. Detection of Genetic Mutation by NGS Mapping 2.1 Plants Under Test and Cultivation Conditions $BC_1S_1$, $BC_2S_1$, $BC_3S_1$ separation populations obtained by crossing the W2939 (TOMJPW2939) strain and the "Micro-Tom" wild strain were tested. The number of tested individuals was as follows: 2 individuals of the $BC_1S_1$ parthenocarpic strain; 13 individuals of the $BC_2S_1$ parthenocarpic strain; 4 individuals of the $BC_3S_1$ parthenocarpic strain; and 23 individuals of the $BC_3S_1$ non-parthenocarpic strain. In order to accurately determine the phenotype, cultivation was carried out by a nutrient film technique using a rockwool cube (Grodan) in a closed cultivation room in the 2D building at the University of Tsukuba. Irrigation was performed daily at 8 am for about 10 minutes. The temperature was maintained at 24° C., and the humidity was maintained at 60 to 70%. A culture solution prepared by using OAT House A formulation (1.5 g/L, OAT House 1; 1 g/L, OAT House 2. OAT Agrio Co., Ltd.) at an electric conductivity (EC) of 1.5 dS/m was used as a hydroponics solution.

2.2 Determination of Parthenocarpy Based on Flower Phenotype

The parthenocarpy was determined based on the flower phenotype at the flowering stage. An individual in which protrusion of styles or anther tube dehiscence due to early enlargement of ovary, and incomplete detachment of petals and styles were observed in floral organs was determined to be a parthenocarpic individual.

2.3 Extraction of Genomic DNA

The Maxwel116 DNA purification Kits (Promega) were used for genomic DNA extraction for NGS mapping in order to increase the purity. About 200 mg of fresh leaf sample was collected in a 1.5 ml Eppendorf tube and frozen with liquid nitrogen, and then the leaf sample was ground using a homogenization pestle. The ground leaf sample in a frozen state was added to Lysis Buffer containing cells of the cartridge in the Kits. A plunger attached to the Kits was inserted into each of the wells, the cartridge was placed in the Maxwel116 (Promega), and then 400 µl of Elution Buffer was applied. After completion of extraction, purification was performed by centrifuging the resultant extract at 6,000 rpm for 3 minutes, transferring a solution from which the precipitates had been removed into another 1.5 ml tube. The concentration of the extracted genomic DNA was measured using NanoDrop (Thermo Fisher Scientific).

2.4 Purification of Genomic DNA

The number of individuals of the $BC_3S_1$ parthenocarpic strain that could be tested was only 4. Thus, in order to further improve the quality of the genomic DNA and increase the accuracy of the whole genome sequencing, these individuals purified by Maxwell were subjected to genomic DNA purification using a Genome-tip column (QIAGEN). 250 µl of the DNA solution of each individual was dispensed into a 1.5 ml tube so that the total amount of DNA was within 30 µg. To the DNA solution, 1 ml of QBT buffer (QIAGEN) was added and mixed. The Genome-tip column was stood in a 15 ml conical tube (Falcon), and 3 ml of QBT buffer was added for equilibration. The column-passed fraction was discarded. Subsequently, a mixed liquid of DNA and QBT was applied to the Genome-tip column, and then 3 ml of QC buffer (QIAGEN) was applied thereto. In case purified DNA was not sufficiently obtained, the passed fractions of these procedures were not discarded but stored. The tube receiving the Genome-tip column was then replaced with a new 15 ml conical tube (Falcon). 2 ml of QF buffer (QIAGEN) warmed to 50° C., in an incubator in advance was applied to the Genome-tip column in 3 portions. To the solution passed through the column, 2 ml of 2-isopropanol was added and mixed, and the mixture was left to stand still at room temperature for 5 minutes. Thereafter, the solution in the conical tube was dispensed into three 2 ml tubes, followed by centrifugation at 13,200 rpm for 15 minutes at 4° C. The tubes after centrifugation were carefully tilted to discard the supernatant, then about 1 ml of 70% ethanol was added, and the mixture was centrifuged at 13,200 rpm for 15 minutes at 4° C. After centrifugation, the tubes were turned upside down and dried in air for 15 minutes. Once the tubes were sufficiently dried, 30 μl of TE buffer was applied and the resultant solution was used for the whole genome sequence.

2.5 Determination of Whole-Genome Sequence by NGS

Whole genome sequencing with NGS was conducted to extract SNPs specific to the W2939 strain. Genomic DNAs of 2 individuals of the parthenocarpic $BC_1S_1$ strain, 13 individuals of the parthenocarpic $BC_2S_1$ strain, 4 individuals of the parthenocarpic $BC_3S_1$ strain, 23 individuals of the non-parthenocarpic $BC_3S_1$ strain were bulked so that the total amount was 5 μl and the resultant samples were subjected to genome resequencing based on short lead assembly. Hi Seq X Ten (Illumina, Inc.) was used as the NGS platform. However, Hi Seq 2000 (Illumina, Inc.) was used in the case of the $BC_1S_1$ strain. Mutations present in the W2939 strain were identified according to the Bowtie2-Samtools-GATK pipeline as described in Pulungun (Plant cell physiology, 2018; 59 (6): 1170-1186). Tomato genome SL3.0 of "Heinz 1706" was used for a reference sequence for resequencing. Tomato genome SL2.50 was used for the $BC_1S_1$ strain. The sequences of the parthenocarpic $BC_2S_1$ and $BC_3S_1$ strains analyzed by resequencing were compared with the sequence of the non-parthenocarpic $BC_3S_1$ strain and the whole genome information of the "Micro-Tom" wild type analyzed in this laboratory, whereby SNPs specific to the mutant parthenocarpic strain were detected. Genetic polymorphisms in the "Micro-Tom" wild type strain were excluded by sequence comparison with the wild type 10 strain. The sequence of the parthenocarpic $BC_1S_1$ strain was compared with the sequences of 3 strains of "Micro-Tom" wild types and 6 strains of another "Micro-Tom" mutants, and mutations found only in this parthenocarpic strain were detected.

2.6 Selection of Candidate Gene Mutation Based on Whole Genome Sequence Results

From the SNPs specific to the parthenocarpic strain detected in 2.5 above, the causative gene mutation was selected under conditions set additionally. Selection was performed only on SNPs that caused non-synonymous amino acid substitutions and had an SNP-index of 1 (allele frequency: 100%), a read depth (number of reads) of 5 or greater, and a (IQ value of 20 or greater, where the value indicates the probability of genotyping. Based on the map-based cloning results, the candidate gene mutation was searched only from chromosome 10. Similar conditions described above were used for specific mutations of the parthenocarpic $BC_1S_1$ and $BC_2S_1$, $BC_3S_1$ strains, and selection was conducted. The results of the strains regarding the selected candidate genes were compared, and the genetic mutations commonly found were examined.

3. Identification of Causative Gene Mutation by Linkage Analysis 3.1 Plants Under Test and Gene to be Tested The $BC_3S_1$ separation population obtained by crossing the W2939 (TOMJPW2939) strain and the "Micro-Tom" wild strain was tested in the linkage analysis. The number of tested individuals was 21 in the case of the parthenocarpic strain and the number of tested individuals was 32 in the case of the non-parthenocarpic strain. The genetic mutation to be subjected to linkage analysis was a candidate gene mutation selected in the $BC_3S_1$ parthenocarpic strain described in 2.4.

3.2 Extraction of Genomic DNA

The Maxwel116 DNA purification Kits (Promega) were used for genomic extraction of the $BC_3S_1$ population. The extraction method is similar to that described in 2.3 above.

3.3 Primer Design

Base sequence information around the SNP was acquired from the physical position of the candidate gene mutation found by resequencing, and the information was input into BLAST search of the Sol Genomics Database to acquire surrounding sequences of about 300 base pairs before and after the SNP. Primers were designed such that about 150 base pairs before and after the SNP could be amplified using a primer design tool: Primer 3. The primers designed were as shown in Table 2.

TABLE 2

Primers Used in Linkage Analysis

| Primer name | Sequence (5' → 3') | SEQ ID NO: |
|---|---|---|
| Solyc10g009590_F247 | CGAAGCACAAGACGTTTTACTTTCT | 21 |
| Solyc10g009590_R248 | CCGAAGCAACGAAAGAAACTAGT | 22 |
| Solyc10g009640_F | TGAAGTTCAAGTTGTTTCGTCTACG | 23 |
| Solyc10g009640_R | TAGAGGTAATTCTCCTGCATAGTGC | 24 |
| Solyc10g019033_F264 | TTCTGAAGGATCCAGCCATGAC | 25 |
| Solyc10g019033_R265 | AACAGCCTTTAACGTCCCAATG | 26 |
| Solyc10g038170_F246 | AGCCCAGAGAAAATAGGCAAGAAT | 27 |
| Solyc10g038170_R78 | GGAAATACGATAACCAGTACCCGA | 28 |

3.4 PCR Reaction

The PCR reaction was conducted using the above-described DNA extract and primers. A PCR enzyme, KOD FX Neo (TOYOBO CO., LTD.), was used. The composition of the reaction solution was: 0.24 μl of KOD FX Neoo (1.0 U/μl), 6 μl of 2×buffer, 2.4 μl of 2 mM dNTPs, 0.24 μl of Fw primer (10 μl), 0.24 μl of Rv primer (10 μl), 2.58 μl of distilled water, and 0.3 μl of template DNA (12 μl in total). PCR conditions were: PCR at 94° C. for 2 minutes, followed by 35 repetition of one cycle of PCR at 98° C., for 10 seconds, 59° C. for 30 seconds, and 68° C. for 30 seconds. Thereafter, PCR was conducted at 68° C. for 7 minutes.

4. Results 4.1 Narrowing of Causative Gene Region by Rough Mapping

In order to narrow down the causative gene region of the W2939 strain, rough mapping in which 2 markers of inter-variety polymorphism were arranged per chromosome was performed as a map-based cloning method. At this time, amplification was performed by PCR using the forward primers and the reverse primers shown in FIG. 5. SNP markers showing polymorphism between "Micro-Tom" and "Regina" were located on the short and long arms of each chromosome, and 12 individuals of the $F_2$ parthenocarpic population obtained by crossing the W2939 strain with the "Regina" wild strain were tested (FIG. 5). As a result, 10 individuals out of 12 individuals showed the genotype of "Micro-Tom" type homo by the marker (2120_1008) located on the short arm of chromosome 10. In the other 23 markers, 8 or less of individuals exhibited the "Micro-Tom" genotype (FIG. 6). Since the parthenocarpy in the individuals of the $F_2$ was considered to be derived from the W2939 strain with which the mutation had been introduced into the "Micro-Tom", it was believed that the causative gene mutation was localized near the marker of the short arm of chromosome 10. It seemed that the causative gene region could be narrowed down by performing fine mapping in which a polymorphic marker was further arranged in this region, but there was no polymorphic marker at a position where the region could be narrowed down. Thus, it was impossible to further narrow down the region. Furthermore, it was believed that the reason why 2 individuals among 12 individuals in the 2120_1008 marker had hetero-genotype was because the genetic distance was far from the causative gene.

4.2 Selection of Candidate Gene Mutation Based on Whole Genome Sequencing Results The W2939 parthenocarpic $BC_1S_1$, $BC_2S_1$, $BC_3S_1$ populations were subjected to whole genome sequencing using NGS, and the reference sequence SL2.50 or SL3.0 were subjected to resequencing. The determined base sequences were compared with the whole genome analysis results of the "Micro-Tom" wild strain and other mutants and the $BC_3S_1$ non-parthenocarpic strain, a gene mutation causing non-synonymous amino acid substitution, having an SNP-index of 1, and having a reliable GQ value was detected. Comparison among total of 9 individuals of the $BC_1S_1$ population, the "Micro-Tom" wild strain, and mutants was performed, and three specific mutations were found on chromosome 10. Furthermore, comparison among total of 32 individuals of the $BC_2S_1$ and $BC_3S_1$ parthenocarpic strains, and the "Micro-Tom" wild strain, mutants, and the $BC_3S_1$ non-parthenocarpic strain was performed, and three and five mutations specific to chromosome 10 were found respectively. Among these mutant-specific gene mutations, a mutant-specific gene mutation in common with the $BC_1S_1$, $BC_2S_1$, and $BC_3S_1$ parthenocarpic strains was examined, and two SNPs on the Solyc10g038170 were extracted. The genomes SL2.50 and SL3.0 differed in terms of their physical positions corresponding to the Solyc10g038170, but the position of mutation introduction was common between the respective strain comparisons. In addition to the Solyc10g038170 on chromosome 10, other chromosomes were also searched in order to confirm whether there were gene mutations commonly detected in all the strains. However, there were no other mutations commonly detected. In order to confirm that two mutations revealed from the results of whole genome sequencing were actually linked to parthenocarpy, linkage analysis by Sanger sequencing was conducted using the $BC_3S_1$ strain backcrossed with the "Micro-Tom" wild strain. As a result, all 21 individuals of the $BC_3S_1$ parthenocarpic strain had the mutant genotype at the mutation site, whereas all 32 individuals of the $BC_3S_1$ non-parthenocarpic strain had the hetero or wild strain genotype. Mutations on the Solyc10g009590, the Solyc10g009640, and the Solyc10g019033 in addition to the Solyc10g038170 were detected as candidates in the $BC_3S_1$ strain where mutations not involved in parthenocarpy should have been excluded mostly. The Solyc10g009590 was estimated to be a tomato homolog of the TRICHOME BIREFRINGENCE-LIKE family gene involved in cellulose synthesis and deposition in secondary cell walls in Arabidopsis thaliana. Also, the Solyc10g009640 was estimated to be a tomato homolog of the Jasmonate resistant 1 (JAR1) gene catalyzing the synthesis of Jasmonoyl-isoleucine (JA-Ile) in Arabidopsis thaliana to induce jasmonic acid (JA) response (Westfall et al., Science, 2012.; 336: 1708-1711). The Solyc10g019033 was an unknown gene that had not been reported to suggest its function in the past. As for the mutations of the three genes, similar individuals were used to perform linkage analysis by Sanger sequencing. 6 out of 21 individuals of the $BC_3S_1$ parthenocarpic strain had the wild type homo-genotype in the case of the Solyc10g009590. 2 out of 32 individuals of the $BC_3S_1$ non-parthenocarpic strain had the mutant type homo-genotype in the case of the Solyc10g009590 and the Solyc10g009640. For the Solyc10g019033, the phenotypes and genotypes of all individuals were linked, similarly to the Solyc10g038170. From these results, the possibility of involvement of the Solyc10g019033 in parthenocarpy could not be eliminated. Accordingly, the expression level in each tissue was examined from the exhaustive transcriptome analysis data by RNA-seq, as described in the following paragraph.

4.3 Selection of Candidate Gene Mutation Based on Transcriptome Analysis Results From the linkage analysis results described in 3.1 above, it was not possible to determine which of the Solyc10g019033 gene and the Solyc10g038170 gene was involved in parthenocarpy or whether both the genes were involved in parthenocarpy. A gene involved in parthenocarpy was assumed to be expressed in the ovary tissue, and RNA-seq was conducted 2 days after flowering, using the ovaries of the BC3S1 parthenocarpic strain and the BC3S1 non-parthenocarpic strain obtained by backcrossing with "Micro-Tom", and the gene expression levels of both strains were used as information for determination. As a result, no Solyc10g019033 was expressed at all in the ovary, but the Solyc10g038170 was slightly expressed in the ovary. From this result, it was not possible to confirm a difference in expression level of Solyc10g038170 between the parthenocarpic strain and the non-parthenocarpic strain (0.03 and 0.02, respectively). The difference in expression level between both genes was small, and thus determination was made incorporating the public data. The Solyc10g019033 was a gene discovered from the tomato genome annotation information ITAG3.0 for the first time. Thus, we referred relatively new analysis data in Tomato functional genomics database in which the gene had been analyzed. As a result, almost no expression was observed in red ripe fruits of the *Solanum lycopersicum* "VF36" and *Solanum* lycopersicoides isogenic strain to be analyzed, and the Reads Per Kilobase of exon per Million mapped reads (RPKM) suggesting the expression level was 0.09 in the most highly expressed strain (LA 4250A). On the basis of this result, the possibility of involvement of the mutation on the Solyc10g019033 in parthenocarpy was considered to be very low. Although the genetic function of the Solyc10g019033 was unknown, the Solyc10g038170 was expected to encode the involvement of the mutation in parthenocarpy at the early stage of JA biosynthesis, according to annotation information. Thus, among the genes analyzed by RNA-seq, the genes associated with the JA function were searched from the DEGs list in which specific expression patterns were found in the parthenocarpic strain. Among the gene groups with increased expression in the parthenocarpic strain, the gene with the second lowest q-value encoded jasmonic acid 2 (JA2) protein, and the gene at position 238 encoded NAC domain protein IPR003441 (JA2-like; JA2L). These genes in the parthenocarpic strain were increased by 4.5 times and 3.8 times, respectively, compared with the gene in the non-parthenocarpic strain. It has been reported that the expression of JA2 is increased by abscisic acid (ABA) treatment, so the JA2 has a role in regulating ABA biosynthesis. Furthermore, the JA2L is a gene whose expression is promoted by JA, and it has been reported that the persistence of stomatal closure resulted in enhanced disease resistance in JA2L antisense individuals, which is common to the jail mutant with deficiency in JA transmission. The functional deficiency of Solyc10g038170 was considered to cause JA biosynthesis, which was different from the results found from the report. However, changes in gene expression pattern resulted from RNA-seq suggested that changes occurred in the JA biosynthesis and transmission pathway in the mutant. Additionally, the gene group in which the expression level in the parthenocarpic strain was reduced to 0.5 times or less, compared with the expression level in the non-parthenocarpic strain, was also examined. As a result, no gene directly associated with the JA was discovered, but there was a notable gene: Gibberellin 2-oxide 2 (GA2ox2) with a small q-value at position 87. This gene is involved in the inactivation of active GA in the GA biosynthetic pathway (Xiao et al., DNA sequence, 2007; 18 (6): 474-479). The expression level of GA2ox2 in the parthenocarpic strain was reduced to about 16%, compared with the non-parthenocarpic strain. This result suggests that, in the parthenocarpic strain, the active GA may be increased, and the GA response and fructification may be promoted. The above-described results showed the possibility of changes in the expression pattern of JA or GA caused by the mutation of the causative gene having parthenocarpy, and the Solyc10g038170 involved in JA biosynthesis was considered to be the most likely candidate causative gene.

4.4 Sequence Analysis of Most Likely Candidate Gene

Figure 8:
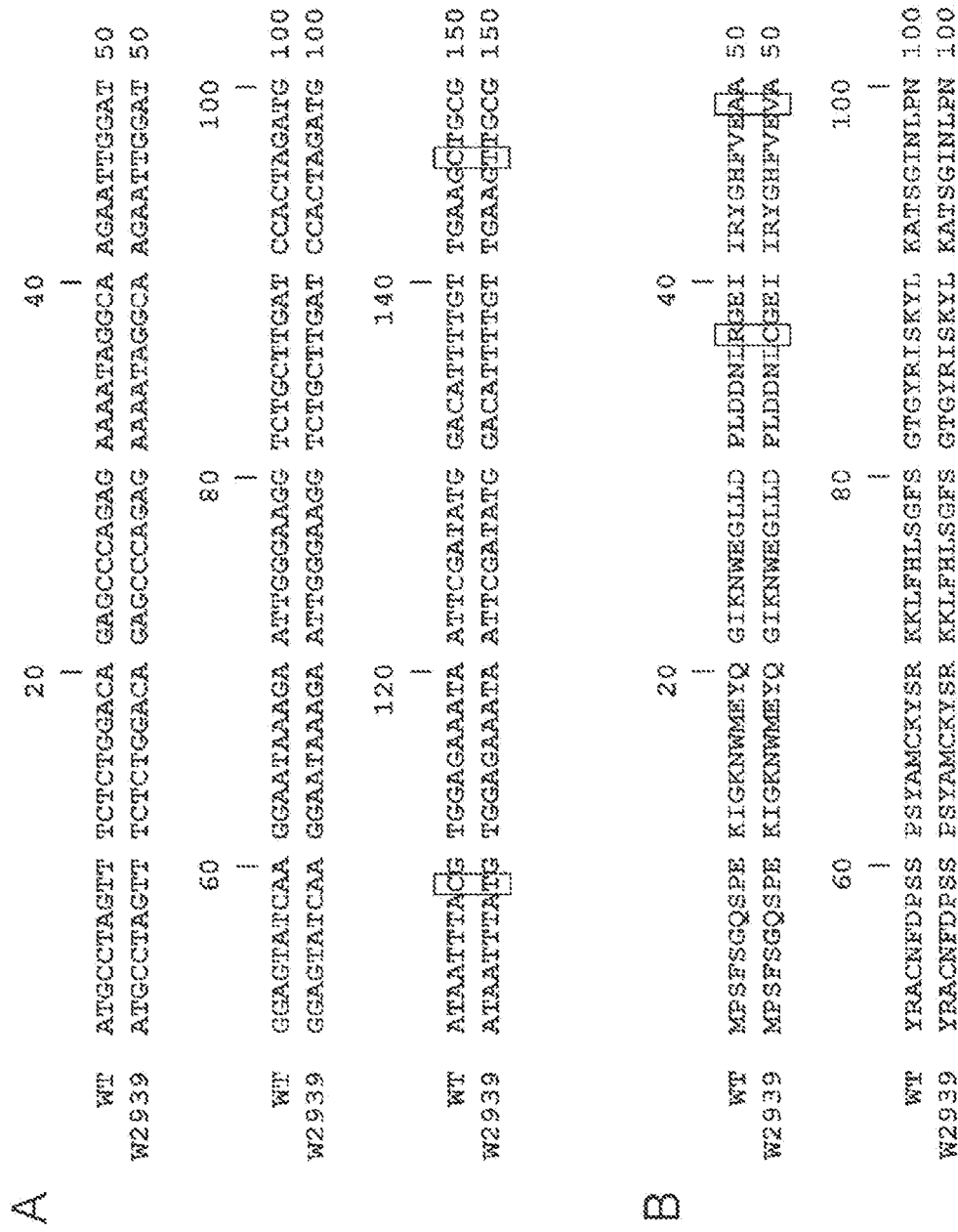
FIGS. 8A and 8B show mutations in the Solyc10g038170 gene of the W2939 strain.

Detailed information of the Solyc10g038170 was searched on the Sol Genomics Network (See https://solgenomics.net/, Nov. 21, 2018), and the gene was estimated to be composed of only 1,131 bp exon (FIG. 7). The Solyc10g038170 is a gene with a total length of 1.131 kbp and consists of only one exon, and the gene has a domain conserved in a class 3 lipase (triglyceride lipase). In the W2939 parthenocarpic strain, a single base substitution is inserted into each base at position 109 and position 146 from the 5' end, resulting in two amino acid missense mutations. Specifically, in the W2939 parthenocarpic strain, a single base substitution mutation "C→T" was confirmed at two positions, and a missense mutation of amino acids in which "arginine" at position 37 (R) was replaced with "cysteine" (C) and "alanine" at position 49 (A) was replaced with "valine" (V) was confirmed (FIG. 8). When it was confirmed whether there was another mutation near the two SNPs, there was no other mutation on the Solyc10g38170. The mutation position closest to the SNPs was an intergenic region of about 13,300 bp upstream of the start sequence of exon. Protein domains were searched using a search tool Pfam. As a result, from proteins at positions 137 to 283, the domain conserved in the class 3 lipase (triglyceride lipase) was confirmed (FIG. 7). However, no mutated position was present in the domain. Alternatively, an ortholog of this gene was searched by the NCBI protein BLAST, and 8 orthologs having a Total Score of 200 or greater and a relatively high homology were discovered. Among them, At2G44810 on chromosome 2 had about 63% amino acid sequence homology, and the homology was significant as compared with At4G16820 (about 45%) having the second highest homology. The amino acid sequence of this ortholog was compared with the amino acid sequence of the Solyc10g038170. As a result, arginine at position 37 among the missense mutations at two positions was common in both the sequences (FIG. 9). Therefore, supposing that this gene is assumed to be a homolog of the Solyc10g038170, it is considered that the arginine at position 37 is more important than the amino acid at position 49 in terms of maintenance of the genetic function, and the mutation of the amino acid residue at position 37 affects the gene expression and the function of the protein after translation.

Example 3

<Production and Characteristics of Solyc10g038170 Gene-Mutated Strain>

I. Determination of Target Sequence

The sgRNA for inducing a mutation in the Solyc10g038170 gene was designed using target sequence search sites for the CRISPR/Cas9 system: CRISPR-P2.0 (See Lei et al., Molecular plant, 2014; 7 (9): 1494-1496) and CRISPRdirect, Naito et al., Bioinformatics, 2015:31 (7): 1120-1123). FIG. 10 shows an example of the Cas9 vector. Two target sequences were set in order to cause a large-scale of mutation in the Solyc10g038170. Furthermore, in order to demonstrate that the mutation generated in the W2939 strain was associated with parthenocarpy, a target sequence present near the mutation site was selected, and individuals having various mutation patterns near the mutation site were expected to be obtained. The selected target sequence at the 5' side (Target1): CCACTAGATGATAATTTACG (SEQ ID NO: 77) had a relatively high On-score of 0.5071 indicating a low off-target effect in CRISPR-P, and contained a site where a single base substitution occurred in the mutant in the sequence. Meanwhile, the selected target sequence at the 3' side (Target2): TATTTGCACATTGCGTATGA (SEQ ID NO: 78) had a relatively low On-score of 0.0405. However, this sequence was close to the site where the single base substitution occurred, and the CRISPRdirect results showed that there was no homologous sequence in 20 bp upstream of the PAM sequence, and the specificity was relatively high even when segments were limited to 12 bp upstream of the PAM sequence. Therefore, the sequence CCACTAGATGA-TAATTTACG (SEQ ID NO: 77) was determined as the target sequence.

2. Production of Solyc10g038170 Gene-Mutated Strain

A vector containing the two target sequences (SEQ ID NOs: 77 and 78) selected in 1. above in an expression cassette was constructed, and an attempt was made to produce a strain in which the function of the Solyc10g038170 gene was knocked out (FIGS. 11 and 12). For transformation of tomatoes, about 200 seeds of the "Micro-Tom" wild strain were tested using the *Agrobacterium* method optimized for "Micro-Tom" (Sun et al., Plant cell physiology, 2006; 47 (3): 426-431). Plant bodies redifferentiated from a series of selection media containing kanamycin were used as transformant candidates, and diploid individuals were selected using a flow cytometer. It was examined whether these individuals had the NPTII region inserted by the Cas9 vector. As a result, insertion of the NPTII region was confirmed in 14 individuals in 11 strains. Furthermore, in order to confirm the double-strand break of DNA by the Cas9 protein and the occurrence of repair errors, the presence or absence of mutation introduction was examined using primers for amplifying the surrounding of the target sequence. As a result, in 8 individuals in 6 strains, a mutation was confirmed to be introduced near the PAM sequence of the Solyc10g038170 gene. Among the obtained 8 individuals in total, 3 individuals in which mutations were homozygously introduced into the Target1 sequence were found. Among them, in the individual of 43-1, a single base insertion mutation was observed at 2 bp upstream from the site where the single base substitution occurred in the W2939 strain. In the individuals of 425-1 and 442-1, biallelic mutations occurred due to the single base insertion and deletion of 2 bases near the single base insertion (FIG. 13).

As a result, a frameshift occurred in the subsequent amino acid sequence, and a termination codon appeared in front of its proper position. The polypeptide that included 376 amino acid residues in the wild strain and the W2939 strain, whereas the polypeptide was estimated to include 47 amino acids in the individual of 43-1, and include 47 or 42 amino acids in the individuals of #25-1 and #42-1 (FIG. 14). In individuals of #9-1, #10-1, and #37-1 among the remaining individuals, a single base insertion was heterozygously introduced at the same position as #3-1, and the other strand was wild type (FIG. 13). In #9-3 and #9-4, a triple waveform was confirmed from the results of Sanger sequencing, which suggested that transformed cells and non-transformed cells co-existed or transformed cells with different mutations co-existed.

The introduction of a mutation in the target sequence Target2 was examined, and the mutation introduction was not confirmed in 7 out of 8 individuals, but mutation with deletion of 7 bases occurred in one of the double strands in #42-1. However, mutations such as large-scale deletion due to the simultaneous introduction of mutations at two positions were not confirmed. The reason why the efficiency of mutation introduction in Target2 was lower than that in Target1 was considered to be that the effectiveness of the sequence of the sgRNA to which the Target2 sequence had been incorporated was low.

3. Phenotype of Solyc10g038170 Gene-Mutated Strain

In the mutated strain, it was considered that changes in the amino acid sequence resulted in functional deficiency of the protein. In the W2939 strain, the protein function was lost by a single base substitution on the Solyc10g038170, and parthenocarpy was induced, and thus the occurrence of parthenocarpy in the mutated strain was also examined. As a result of examination of the phenotype at flowering stage, a phenotype such as early enlargement of ovary, protrusion of styles, discoloration of anther tube tip, or remained petals or styles after the ovary enlargement was confirmed in all the mutated individuals in which mutations were homozygously introduced. These phenotypes were common to the W2939 parthenocarpic strain. Seedless red ripe fruits were often observed in the mutated individual. The phenotype of transformant having mutated gene, but having no mutation was also examined for comparison. Consequently, in contrast to the mutated individual, the phenotype of flower was similar to that of the wild strain, and all the red ripe fruits had 11 or more seeds. These results suggested that parthenocarpy was induced by the mutation in the Solyc10g038170 gene confirmed in the mutated strain. Thus, this gene was inferred to be a novel parthenocarpy-related gene.

4. Analysis of Expression Level of S1DAD1 Gene

The transcriptome analysis conducted in the past suggests that the S1DAD1 (another name: Solyc10g038170) gene is specifically expressed in buds before flowering. Therefore, in order to confirm that the expression level of S1DAD1 gene was suppressed in the buds of the W2939 parthenocarpic strain and to suggest the possibility of such suppression affecting the JA biosynthesis, the expression level was analyzed for each tissue using the "Micro-Tom" wild strain and the W2939 non-parthenocarpic strains and parthenocarpic strains. As a result of measuring the expression level by the qRT-PCR method, the expression level of each of the tissues in the wild strain was extremely low at the 4-mm bud stage and on the flowering date, but the expression level was greatly increased in the petal sample 2 days before flowering. In the sampling method of the present example, tomato filaments were included in the petal sample because its tissues were partially attached to the petals. Based on this fact, as shown in the ortholog At2G44810 of Arabidopsis thaliana (FIG. 9), the S1DAD1 gene may be transiently expressed in the flower filaments at this developmental stage (Ishiguro et al., The plant cell, 2001; 13 (10): 2191-2209; Klepikova et al., The plant journal, 2016; 88 (6): 1058-1070). Meanwhile, in the W2939 parthenocarpic strain, the expression level of the petal sample 2 days before flowering was significantly reduced to approximately 1%, compared with the wild strain. In the W2939 non-parthenocarpic strain, the expression level was also reduced to about 38%, but no significant difference was observed. Considering that the single base substitution mutation introduced into the S1DAD1 gene by EMS was not present at any position other than the two positions described above, it is believed that the expression of the S1DAD1 gene was suppressed by SNPs at the two positions.

The results of the above-described experiment are summarized as follows.

The causative gene having parthenocarpy of the tomato W2939 strain is the Solyc10g038170 (another name: S1dad1) gene on chromosome 10, which is a gene with a total length of 1131 bp and consists of only one exon, and has a domain conserved in a class 3 lipase (triglyceride lipase). It was revealed this time that the causative gene mutation of the W2939 parthenocarpic strain was the substitution mutation "C→T" of bases at position 109 and position 146 from the 5' end, i.e., a missense mutation of amino acids in which "arginine" at position 37 (R) was replaced with "cysteine" (C) and "alanine" at position 49 (A) was replaced with "valine" (V).

A comparison between phenotypes of a wild strain of tomato and a plant body into which the S1dad1 mutation was introduced by the CRISPR/Cas9 system was performed in terms of the parthenocarpic rate and yield in the summer season (under high temperature stress conditions). Furthermore, the flowers before flowering were emasculated, and then the proportion of stamens in mature intraspecific fruits was examined. As a result, the parthenocarpic rate was 57.1% in the wild strain, whereas the parthenocarpic rate was as high as 99.4% in the plant with the S1dad1 mutation. Furthermore, the yields of the wild strain and the plant having the S1dad1 mutation were compared based on the total weight of red-ripened mature fruits. The wild strain had a yield of 26.3±2.7 g, whereas the plant having the S1dad1 mutation had a yield of 63.1±2.5 g. Thus, the plant having the S1dad1 mutation exhibited high fructification rate and high temperature resistance.

INDUSTRIAL APPLICABILITY

Although vibration stimulation, treatment with plant hormone agents, or use of insect vectors are required for flowers in bloom in order to achieve fructification stability in known tomato cultivation, a reduction in labor is achieved by using the mutation of the present invention that induces parthenocarpy. Furthermore, cultivation can be conducted even at high temperatures, thus contributing to an increase in cultivation period or cultivation area. Consequently, it is possible to develop varieties for labor-saving cultivation using the plant mutant according to the present invention as a breeding material, which leads to year-round stable production of tomatoes for raw consumption and processing. Furthermore, the use of this genetic mutation information makes it possible to develop varieties with parthenocarpy and high temperature resistance, in not only tomatoes but also in other fruit vegetables.

SEQUENCE LISTING FREE TEXT

SEQ ID NO: 3: Nucleotide sequence of Solyc10g038170 gene mutant

SEQ ID NO: 4: Amino acid sequence of Solyc10g038170 protein mutant

SEQ ID NO: 6: Partial nucleotide sequence of Solyc10g038170 gene mutant (nucleotide number 1 to 150)

SEQ ID NO: 8: Partial amino acid sequence of Solyc10g038170 protein mutant (amino acid number 1 to 80)

SEQ ID NOs: 15 to 16: Nucleotide sequence of target 1 region of T0-mutated strain (FIG. 13)

SEQ ID NOs: 18 to 20: Amino acid sequence of target 1 region of T0-mutated strain (FIG. 14)

SEQ ID NOs: 21 to 76: Primers

All publications, patents and patent applications cited in the present specification are incorporated herein by reference in their entirety.

Sequence Listing

The invention claimed is:

1. A tomato plant exhibiting parthenocarpy or a portion thereof comprising a mutation in a Solyc10g038170 gene, the mutation causing deficiency or reduction in expression of a protein encoded by the Solyc10g038170 gene,
wherein the gene is a polynucleotide encoding a protein comprising the amino acid sequence of SEQ ID NO: 2, and
wherein the mutation of the gene comprises the nucleotide sequence encoding the amino acid sequence comprising a substitution of arginine at position 37 in the amino acid sequence of SEQ ID NO: 2 with cysteine and a substitution of alanine at position 49 in the amino acid sequence of SEQ ID NO: 2 with valine.

2. The tomato plant or the portion thereof according to claim 1, comprising a parthenocarpic rate of 95% or greater.

3. The tomato plant or the portion thereof according to claim 1, wherein the tomato plant or the portion thereof is resistant to an ambient temperature of 30° C. or higher.

4. The tomato plant or the portion thereof according to claim 1, wherein the tomato plant is homozygous for the mutation.

5. A method for producing the tomato plant according to claim 1, comprising:
(1) introducing a mutation of a Solyc10g038170 gene into a cell, callus or tissue of a wild type of the tomato plant, the mutation causing deficiency or reduction in expression of the Solyc10g038170 gene;
(2) culturing the cell, callus or tissue of the tomato plant in the step (1) to form a tomato plant body population; and
(3) selecting a tomato plant having parthenocarpy from the tomato plant body population in the step (2),
wherein the gene is a polynucleotide encoding a protein comprising the amino acid sequence of SEQ ID NO: 2, and
wherein the mutation is performed by introducing a polynucleotide comprising the nucleotide sequence of SEQ ID NO: 3 in the nucleotide sequence of SEQ ID NO: 1 of the Solyc10g038170 gene.

6. The method according to claim 5, wherein the tomato plant selected in the step (3) is homozygous for the mutation.

7. A polynucleotide comprising the nucleotide sequence of SEQ ID NO: 3.

8. A method for selecting a parthenocarpic tomato plant from tomato plants, the method comprising:
(1) detecting a mutation causing deficiency or reduction in expression of a protein encoded by a Solyc10g038170 gene in a cell or tissue of a tomato plant; and
(2) selecting the parthenocarpic tomato plant from the tomato plants on the basis of the presence of the mutation as detected in the step (1),
wherein the gene is a polynucleotide encoding a protein comprising the amino acid sequence of SEQ ID NO: 2, and
wherein the fruit bearing plant is a Solanaceae plant wherein the mutation of the gene comprises the nucleotide sequence encoding the amino acid sequence comprising a substitution of arginine at position 37 in the amino acid sequence of SEQ ID NO: 2 with cysteine and a substitution of alanine at position 49 in the amino acid sequence of SEQ ID NO: 2 with valine.

9. The method according to claim 8, wherein the detection is performed by PCR or hybridization.

* * * * *

```
SEQUENCE LISTING

<160> NUMBER OF SEQ ID NOS: 96

<210> SEQ ID NO 1
<211> LENGTH: 1131
<212> TYPE: DNA
<213> ORGANISM: Solanum lycopersicum L.

<400> SEQUENCE: 1
atgcctagtt tctctggaca gagcccagag aaaataggca agaattggat ggagtatcaa     60
ggaataaaga attgggaagg tctgcttgat ccactagatg ataatttacg tggagaaata    120
attcgatatg gacattttgt tgaagctgcg tacagagcat gcaattttga tccttcttct    180
ccttcatacg caatgtgcaa atactcgaga agaaaattgt ttcatctttc tggcttttcg    240
ggtactggtt atcgtatttc caagtacttg aaagctacta gtgggattaa tcttccaaat    300
tgggttgata aagctcctaa atggatgtca aagcaatcaa gttggattgg ttatgttgcg    360
atttgtcatg accaaagaga aatagcaaga ctagggagaa gagacgttgt tattgcctta    420
cgaggcacag caacttgttt agagtggctc gagaatctac gagccactct aactcctctc    480
cctaacatta aacataccat atgttgcccg atggttgaaa gtggtttcct aagtttatat    540
acatccaaaa tagacgcgca acagagtcta caagacatgg ttagagaaga aatagaccga    600
attaaaaaat tatacgatgg tgaaacttta agcttcacta tcgcaggtca ctcccttggg    660
gccgcgttag cgactctaac agcctatgat attaaacaat ttttcagaga tataccacta    720
gtaacagtca tgtcctttgg tggtccaaga gttggaaacc atagttttcg ataccatctt    780
gacaaacaag ataccaaaat tttgcgtatc gtcaactcag acgatcttat aacaaaaatt    840
cctggattcg tcattgacaa caatgacgat gatgataaat atgtggaaaa aagtgatcac    900
tggatgaaaa ggcttgtgga agatagtcaa tgggtatatg cagatgttgg atgtgagtta    960
cgtttaagta gtagtggttc accacctttt aatgggatta atattgcaac ttgtcatgaa   1020
ttaaatactt atcttcattt agttaatagt tttgttagct caagttgtcc tgttagagct   1080
actgcaaaaa aaattatgca caaagtaac aataatgtaa aatgtacgta a              1131

<210> SEQ ID NO 2
<211> LENGTH: 376
<212> TYPE: PRT
<213> ORGANISM: Solanum lycopersicum L.

<400> SEQUENCE: 2

Met Pro Ser Phe Ser Gly Gln Ser Pro Glu Lys Ile Gly Lys Asn Trp
```

```
1               5                   10                  15
Met Glu Tyr Gln Gly Ile Lys Asn Trp Glu Gly Leu Leu Asp Pro Leu
                20                  25                  30
Asp Asp Asn Leu Arg Gly Glu Ile Ile Arg Tyr Gly His Phe Val Glu
            35                  40                  45
Ala Ala Tyr Arg Ala Cys Asn Phe Asp Pro Ser Ser Pro Ser Tyr Ala
        50                  55                  60
Met Cys Lys Tyr Ser Arg Lys Lys Leu Phe His Leu Ser Gly Phe Ser
65                  70                  75                  80
Gly Thr Gly Tyr Arg Ile Ser Lys Tyr Leu Lys Ala Thr Ser Gly Ile
                85                  90                  95
Asn Leu Pro Asn Trp Val Asp Lys Ala Pro Lys Trp Met Ser Lys Gln
            100                 105                 110
Ser Ser Trp Ile Gly Tyr Val Ala Ile Cys His Asp Gln Arg Glu Ile
        115                 120                 125
Ala Arg Leu Gly Arg Arg Asp Val Val Ile Ala Leu Arg Gly Thr Ala
    130                 135                 140
Thr Cys Leu Glu Trp Leu Glu Asn Leu Arg Ala Thr Leu Thr Pro Leu
145                 150                 155                 160
Pro Asn Ile Lys His Thr Ile Cys Cys Pro Met Val Glu Ser Gly Phe
                165                 170                 175
Leu Ser Leu Tyr Thr Ser Lys Ile Asp Ala Gln Gln Ser Leu Gln Asp
            180                 185                 190
Met Val Arg Glu Glu Ile Asp Arg Ile Lys Lys Leu Tyr Asp Gly Glu
        195                 200                 205
Thr Leu Ser Phe Thr Ile Ala Gly His Ser Leu Gly Ala Ala Leu Ala
210                 215                 220
Thr Leu Thr Ala Tyr Asp Ile Lys Gln Phe Phe Arg Asp Ile Pro Leu
225                 230                 235                 240
Val Thr Val Met Ser Phe Gly Gly Pro Arg Val Gly Asn His Ser Phe
                245                 250                 255
Arg Tyr His Leu Asp Lys Gln Asp Thr Lys Ile Leu Arg Ile Val Asn
            260                 265                 270
Ser Asp Asp Leu Ile Thr Lys Ile Pro Gly Phe Val Ile Asp Asn Asn
        275                 280                 285
Asp Asp Asp Lys Tyr Val Glu Lys Ser Asp His Trp Met Lys Arg
    290                 295                 300
Leu Val Glu Asp Ser Gln Trp Val Tyr Ala Asp Val Gly Cys Glu Leu
305                 310                 315                 320
Arg Leu Ser Ser Gly Ser Pro His Phe Asn Gly Ile Asn Ile Ala
                325                 330                 335
Thr Cys His Glu Leu Asn Thr Tyr Leu His Leu Val Asn Ser Phe Val
            340                 345                 350
Ser Ser Ser Cys Pro Val Arg Ala Thr Ala Lys Lys Ile Met His Lys
        355                 360                 365
Ser Asn Asn Asn Val Lys Cys Thr
    370                 375

<210> SEQ ID NO 3
<211> LENGTH: 1131
<212> TYPE: DNA
<213> ORGANISM: Artificial
<220> FEATURE:
<223> OTHER INFORMATION: Mutant of Solyc10g038170 gene
```

<400> SEQUENCE: 3

```
atgcctagtt tctctggaca gagcccagag aaaataggca agaattggat ggagtatcaa      60
ggaataaaga attgggaagg tctgcttgat ccactagatg ataatttatg tggagaaata     120
attcgatatg gcattttgt tgaagttgcg tacagagcat gcaattttga tccttcttct     180
ccttcatacg caatgtgcaa atactcgaga agaaattgt ttcatctttc tggcttttcg     240
ggtactggtt atcgtatttc caagtacttg aaagctacta gtgggattaa tcttccaaat     300
tgggttgata agctcctaa atggatgtca agcaatcaa gttggattgg ttatgttgcg     360
atttgtcatg accaaagaga atagcaaga ctagggagaa gagacgttgt tattgcctta     420
cgaggcacag caacttgttt agagtggctc gagaatctac gagccactct aactcctctc     480
cctaacatta aacataccat atgttgcccg atggttgaaa gtggtttcct aagtttatat     540
acatccaaaa tagacgcgca acagagtcta caagacatgg ttagagaaga aatagaccga     600
attaaaaaat tatacgatgg tgaaacttta agcttcacta tcgcaggtca ctcccttggg     660
gccgcgttag cgactctaac agcctatgat attaaacaat ttttcagaga tataccacta     720
gtaacagtca tgtcctttgg tggtccaaga gttggaaacc atagttttcg ataccatctt     780
gacaaacaag ataccaaaat tttgcgtatc gtcaactcag acgatcttat aacaaaaatt     840
cctggattcg tcattgacaa caatgacgat gatgataaat atgtggaaaa agtgatcac     900
tggatgaaaa ggcttgtgga agatagtcaa tgggtatatg cagatgttgg atgtgagtta     960
cgtttaagta gtagtggttc accacacttt aatgggatta atattgcaac ttgtcatgaa    1020
ttaaatactt atcttcattt agttaatagt tttgttagct caagttgtcc tgttagagct    1080
actgcaaaaa aaattatgca caaagtaac aataatgtaa aatgtacgta a              1131
```

<210> SEQ ID NO 4
<211> LENGTH: 376
<212> TYPE: PRT
<213> ORGANISM: Artificial
<220> FEATURE:
<223> OTHER INFORMATION: Mutant of Solyc10g038170 protein

<400> SEQUENCE: 4

```
Met Pro Ser Phe Ser Gly Gln Ser Pro Glu Lys Ile Gly Lys Asn Trp
  1               5                  10                  15

Met Glu Tyr Gln Gly Ile Lys Asn Trp Glu Gly Leu Leu Asp Pro Leu
             20                  25                  30

Asp Asp Asn Leu Cys Gly Glu Ile Ile Arg Tyr Gly His Phe Val Glu
         35                  40                  45

Val Ala Tyr Arg Ala Cys Asn Phe Asp Pro Ser Ser Pro Ser Tyr Ala
     50                  55                  60

Met Cys Lys Tyr Ser Arg Lys Lys Leu Phe His Leu Ser Gly Phe Ser
 65                  70                  75                  80

Gly Thr Gly Tyr Arg Ile Ser Lys Tyr Leu Lys Ala Thr Ser Gly Ile
                 85                  90                  95

Asn Leu Pro Asn Trp Val Asp Lys Ala Pro Lys Trp Met Ser Lys Gln
            100                 105                 110

Ser Ser Trp Ile Gly Tyr Val Ala Ile Cys His Asp Gln Arg Glu Ile
        115                 120                 125

Ala Arg Leu Gly Arg Arg Asp Val Val Ile Ala Leu Arg Gly Thr Ala
    130                 135                 140

Thr Cys Leu Glu Trp Leu Glu Asn Leu Arg Ala Thr Leu Thr Pro Leu
145                 150                 155                 160
```

```
Pro Asn Ile Lys His Thr Ile Cys Cys Pro Met Val Glu Ser Gly Phe
            165                 170                 175

Leu Ser Leu Tyr Thr Ser Lys Ile Asp Ala Gln Gln Ser Leu Gln Asp
            180                 185                 190

Met Val Arg Glu Glu Ile Asp Arg Ile Lys Lys Leu Tyr Asp Gly Glu
            195                 200                 205

Thr Leu Ser Phe Thr Ile Ala Gly His Ser Leu Gly Ala Ala Leu Ala
            210                 215                 220

Thr Leu Thr Ala Tyr Asp Ile Lys Gln Phe Phe Arg Asp Ile Pro Leu
225                 230                 235                 240

Val Thr Val Met Ser Phe Gly Gly Pro Arg Val Gly Asn His Ser Phe
            245                 250                 255

Arg Tyr His Leu Asp Lys Gln Asp Thr Lys Ile Leu Arg Ile Val Asn
            260                 265                 270

Ser Asp Asp Leu Ile Thr Lys Ile Pro Gly Phe Val Ile Asp Asn Asn
            275                 280                 285

Asp Asp Asp Lys Tyr Val Glu Lys Ser Asp His Trp Met Lys Arg
    290                 295                 300

Leu Val Glu Asp Ser Gln Trp Val Tyr Ala Asp Val Gly Cys Glu Leu
305                 310                 315                 320

Arg Leu Ser Ser Ser Gly Ser Pro His Phe Asn Gly Ile Asn Ile Ala
            325                 330                 335

Thr Cys His Glu Leu Asn Thr Tyr Leu His Leu Val Asn Ser Phe Val
            340                 345                 350

Ser Ser Ser Cys Pro Val Arg Ala Thr Ala Lys Lys Ile Met His Lys
            355                 360                 365

Ser Asn Asn Asn Val Lys Cys Thr
            370                 375

<210> SEQ ID NO 5
<211> LENGTH: 150
<212> TYPE: DNA
<213> ORGANISM: Solanum lycopersicum L.

<400> SEQUENCE: 5
atgcctagtt tctctggaca gagcccagag aaaataggca agaattggat ggagtatcaa    60
ggaataaaga attgggaagg tctgcttgat ccactagatg ataatttacg tggagaaata   120
attcgatatg gacattttgt tgaagctgcg                                    150

<210> SEQ ID NO 6
<211> LENGTH: 150
<212> TYPE: DNA
<213> ORGANISM: Artificial
<220> FEATURE:
<223> OTHER INFORMATION: Partial nucleotide sequence of Solyc10g038170
      gene mutant

<400> SEQUENCE: 6
atgcctagtt tctctggaca gagcccagag aaaataggca agaattggat ggagtatcaa    60
ggaataaaga attgggaagg tctgcttgat ccactagatg ataatttatg tggagaaata   120
attcgatatg gacattttgt tgaagttgcg                                    150

<210> SEQ ID NO 7
<211> LENGTH: 100
<212> TYPE: PRT
<213> ORGANISM: Solanum lycopersicum L.
```

<400> SEQUENCE: 7

Met Pro Ser Phe Ser Gly Gln Ser Pro Glu Lys Ile Gly Lys Asn Trp
1               5                   10                  15

Met Glu Tyr Gln Gly Ile Lys Asn Trp Glu Gly Leu Leu Asp Pro Leu
            20                  25                  30

Asp Asp Asn Leu Arg Gly Glu Ile Ile Arg Tyr Gly His Phe Val Glu
        35                  40                  45

Ala Ala Tyr Arg Ala Cys Asn Phe Asp Pro Ser Ser Pro Ser Tyr Ala
    50                  55                  60

Met Cys Lys Tyr Ser Arg Lys Lys Leu Phe His Leu Ser Gly Phe Ser
65                  70                  75                  80

Gly Thr Gly Tyr Arg Ile Ser Lys Tyr Leu Lys Ala Thr Ser Gly Ile
                85                  90                  95

Asn Leu Pro Asn
            100

<210> SEQ ID NO 8
<211> LENGTH: 100
<212> TYPE: PRT
<213> ORGANISM: Artificial
<220> FEATURE:
<223> OTHER INFORMATION: Partial amino acid sequence of Solyc10g038170
      protein mutant

<400> SEQUENCE: 8

Met Pro Ser Phe Ser Gly Gln Ser Pro Glu Lys Ile Gly Lys Asn Trp
1               5                   10                  15

Met Glu Tyr Gln Gly Ile Lys Asn Trp Glu Gly Leu Leu Asp Pro Leu
            20                  25                  30

Asp Asp Asn Leu Cys Gly Glu Ile Ile Arg Tyr Gly His Phe Val Glu
        35                  40                  45

Val Ala Tyr Arg Ala Cys Asn Phe Asp Pro Ser Ser Pro Ser Tyr Ala
    50                  55                  60

Met Cys Lys Tyr Ser Arg Lys Lys Leu Phe His Leu Ser Gly Phe Ser
65                  70                  75                  80

Gly Thr Gly Tyr Arg Ile Ser Lys Tyr Leu Lys Ala Thr Ser Gly Ile
                85                  90                  95

Asn Leu Pro Asn
            100

<210> SEQ ID NO 9
<211> LENGTH: 80
<212> TYPE: PRT
<213> ORGANISM: Solanum lycopersicum L.

<400> SEQUENCE: 9

Met Pro Ser Phe Ser Gly Gln Ser Pro Glu Lys Ile Gly Lys Asn Trp
1               5                   10                  15

Met Glu Tyr Gln Gly Ile Lys Asn Trp Glu Gly Leu Leu Asp Pro Leu
            20                  25                  30

Asp Asp Asn Leu Arg Gly Glu Ile Ile Arg Tyr Gly His Phe Val Glu
        35                  40                  45

Ala Ala Tyr Arg Ala Cys Asn Phe Asp Pro Ser Ser Pro Ser Tyr Ala
    50                  55                  60

Met Cys Lys Tyr Ser Arg Lys Lys Leu Phe His Leu Ser Gly Phe Ser
65                  70                  75                  80

<210> SEQ ID NO 10
<211> LENGTH: 64
<212> TYPE: PRT
<213> ORGANISM: Arabidopsis thaliana

<400> SEQUENCE: 10

Met Glu Tyr Gln Gly Leu Gln Asn Trp Asp Gly Leu Leu Asp Pro Leu
1               5                   10                  15

Asp Asp Asn Leu Arg Arg Glu Ile Leu Arg Tyr Gly Gln Phe Val Glu
            20                  25                  30

Ser Ala Tyr Gln Ala Phe Asp Phe Asp Pro Ser Ser Pro Thr Tyr Gly
        35                  40                  45

Thr Cys Arg Phe Pro Arg Ser Thr Leu Leu Glu Arg Ser Gly Leu Pro
    50                  55                  60

<210> SEQ ID NO 11
<211> LENGTH: 300
<212> TYPE: DNA
<213> ORGANISM: Solanum lycopersicum L.

<400> SEQUENCE: 11
atgcctagtt tctctggaca gagcccagag aaaataggca agaattggat ggagtatcaa      60
ggaataaaga attgggaagg tctgcttgat ccactagatg ataatttacg tggagaaata     120
attcgatatg gacattttgt tgaagctgcg tacagagcat gcaattttga tccttcttct     180
ccttcatacg caatgtgcaa atactcgaga agaaattgt ttcatctttc tggcttttcg      240
ggtactggtt atcgtatttc caagtacttg aaagctacta gtgggattaa tcttccaaat     300

<210> SEQ ID NO 12
<211> LENGTH: 300
<212> TYPE: DNA
<213> ORGANISM: Solanum lycopersicum L.

<400> SEQUENCE: 12
tacggatcaa agagacctgt ctcgggtctc ttttatccgt tcttaaccta cctcatagtt      60
ccttatttct taaccttcc agacgaacta ggtgatctac tattaaatgc acctcttat      120 taagctatac ctgtaaaaca acttcgacgc atgtctcgta cgttaaaact aggaagaaga     180
ggaagtatgc gttacacgtt tatgagctct tcctttaaca agtagaaag accgaaaagc     240 ccatgaccaa tagcataaag gttcatgaac tttcgatgat caccctaatt agaaggttta     300

<210> SEQ ID NO 13
<211> LENGTH: 100
<212> TYPE: PRT
<213> ORGANISM: Solanum lycopersicum L.

<400> SEQUENCE: 13

Met Pro Ser Phe Ser Gly Gln Ser Pro Glu Lys Ile Gly Lys Asn Trp
1               5                   10                  15

Met Glu Tyr Gln Gly Ile Lys Asn Trp Glu Gly Leu Leu Asp Pro Leu
            20                  25                  30

Asp Asp Asn Leu Arg Gly Glu Ile Ile Arg Tyr Gly His Phe Val Glu
        35                  40                  45

Ala Ala Tyr Arg Ala Cys Asn Phe Asp Pro Ser Ser Pro Ser Tyr Ala
    50                  55                  60

Met Cys Lys Tyr Ser Arg Lys Lys Leu Phe His Leu Ser Gly Phe Ser
65                  70                  75                  80

Gly Thr Gly Tyr Arg Ile Ser Lys Tyr Leu Lys Ala Thr Ser Gly Ile
            85                  90                  95

Asn Leu Pro Asn
            100

<210> SEQ ID NO 14
<211> LENGTH: 33
<212> TYPE: DNA
<213> ORGANISM: Solanum lycopersicum L.

<400> SEQUENCE: 14
ttgatccact agatgataat ttacgtggag aaa                                33

<210> SEQ ID NO 15
<211> LENGTH: 34
<212> TYPE: DNA
<213> ORGANISM: Artificial
<220> FEATURE:
<223> OTHER INFORMATION: Nucleotide sequence of target 1 region of T0
      mutation-bearing lineage

<400> SEQUENCE: 15
ttgatccact agatgataat tttacgtgga gaaa                               34

<210> SEQ ID NO 16
<211> LENGTH: 31
<212> TYPE: DNA
<213> ORGANISM: Artificial
<220> FEATURE:
<223> OTHER INFORMATION: Nucleotide sequence of target 1 region of T0
      mutation-bearing lineage

<400> SEQUENCE: 16
ttgatccact agatgataat acgtggagaa a                                  31

<210> SEQ ID NO 17
<211> LENGTH: 20
<212> TYPE: PRT
<213> ORGANISM: Solanum lycopersicum L.

<400> SEQUENCE: 17

Leu Asp Asp Asn Leu Arg Gly Glu Ile Ile Arg Tyr Gly His Phe Val
1               5                   10                  15

Glu Ala Ala Tyr
            20

<210> SEQ ID NO 18
<211> LENGTH: 20
<212> TYPE: PRT
<213> ORGANISM: Artificial
<220> FEATURE:
<223> OTHER INFORMATION: Amino acid sequence of target 1 region of T0
      mutation-bearing lineage

<400> SEQUENCE: 18

Leu Asp Asp Asn Leu Cys Gly Glu Ile Ile Arg Tyr Gly His Phe Val
1               5                   10                  15

Glu Ala Ala Tyr
            20

<210> SEQ ID NO 19
<211> LENGTH: 16
<212> TYPE: PRT
<213> ORGANISM: Artificial
<220> FEATURE:

<223> OTHER INFORMATION: Amino acid sequence of target 1 region of T0
      mutation-bearing lineage

<400> SEQUENCE: 19

Leu Asp Asp Asn Phe Thr Trp Arg Asn Asn Ser Ile Trp Thr Phe Cys
1               5                   10                  15

<210> SEQ ID NO 20
<211> LENGTH: 11
<212> TYPE: PRT
<213> ORGANISM: Artificial
<220> FEATURE:
<223> OTHER INFORMATION: Amino acid sequence of target 1 region of T0
      mutation-bearing lineage

<400> SEQUENCE: 20

Leu Asp Asp Asn Thr Arg Lys Asn Tyr Ser Arg
1               5                   10

<210> SEQ ID NO 21
<211> LENGTH: 24
<212> TYPE: DNA
<213> ORGANISM: Artificial
<220> FEATURE:
<223> OTHER INFORMATION: Primer

<400> SEQUENCE: 21
cgaagcacaa gacgtttact ttct                                          24

<210> SEQ ID NO 22
<211> LENGTH: 24
<212> TYPE: DNA
<213> ORGANISM: Artificial
<220> FEATURE:
<223> OTHER INFORMATION: Primer

<400> SEQUENCE: 22
ccgaagcaac gaaagaaaac tagt                                          24

<210> SEQ ID NO 23
<211> LENGTH: 25
<212> TYPE: DNA
<213> ORGANISM: Artificial
<220> FEATURE:
<223> OTHER INFORMATION: Primer

<400> SEQUENCE: 23
tgaagttcaa gttgtttcgt ctacg                                         25

<210> SEQ ID NO 24
<211> LENGTH: 25
<212> TYPE: DNA
<213> ORGANISM: Artificial
<220> FEATURE:
<223> OTHER INFORMATION: Primer

<400> SEQUENCE: 24
tagaggtaat tctcctgcat agtgc                                         25

<210> SEQ ID NO 25
<211> LENGTH: 22
<212> TYPE: DNA
<213> ORGANISM: Artificial
<220> FEATURE:
<223> OTHER INFORMATION: Primer

<400> SEQUENCE: 25

-continued ttctgaagga tccagccatg ac                                          22

<210> SEQ ID NO 26
<211> LENGTH: 22
<212> TYPE: DNA
<213> ORGANISM: Artificial
<220> FEATURE:
<223> OTHER INFORMATION: Primer

<400> SEQUENCE: 26
aacagccttt aacgtcccaa tg                                          22

<210> SEQ ID NO 27
<211> LENGTH: 24
<212> TYPE: DNA
<213> ORGANISM: Artificial
<220> FEATURE:
<223> OTHER INFORMATION: Primer

<400> SEQUENCE: 27
agcccagaga aataggcaa gaat                                         24

<210> SEQ ID NO 28
<211> LENGTH: 24
<212> TYPE: DNA
<213> ORGANISM: Artificial
<220> FEATURE:
<223> OTHER INFORMATION: Primer

<400> SEQUENCE: 28
ggaaatacga taaccagtac ccga                                        24

<210> SEQ ID NO 29
<211> LENGTH: 22
<212> TYPE: DNA
<213> ORGANISM: Artificial
<220> FEATURE:
<223> OTHER INFORMATION: Primer

<400> SEQUENCE: 29
ttggagtaaa catcggcact ga                                          22

<210> SEQ ID NO 30
<211> LENGTH: 22
<212> TYPE: DNA
<213> ORGANISM: Artificial
<220> FEATURE:
<223> OTHER INFORMATION: Primer

<400> SEQUENCE: 30
aaccaaaact ggtgcagcat tt                                          22

<210> SEQ ID NO 31
<211> LENGTH: 25
<212> TYPE: DNA
<213> ORGANISM: Artificial
<220> FEATURE:
<223> OTHER INFORMATION: Primer

<400> SEQUENCE: 31
attgggctac ttcaggtgga aaata                                       25

<210> SEQ ID NO 32
<211> LENGTH: 25
<212> TYPE: DNA

<213> ORGANISM: Artificial
<220> FEATURE:
<223> OTHER INFORMATION: Primer

<400> SEQUENCE: 32
tccgtggtgc ttgtttataa acttc                        25

<210> SEQ ID NO 33
<211> LENGTH: 25
<212> TYPE: DNA
<213> ORGANISM: Artificial
<220> FEATURE:
<223> OTHER INFORMATION: Primer

<400> SEQUENCE: 33
gtttcaaccc aaaccaaatc caatg                        25

<210> SEQ ID NO 34
<211> LENGTH: 25
<212> TYPE: DNA
<213> ORGANISM: Artificial
<220> FEATURE:
<223> OTHER INFORMATION: Primer

<400> SEQUENCE: 34
caattgaagt acctgtgaca aatgc                        25

<210> SEQ ID NO 35
<211> LENGTH: 22
<212> TYPE: DNA
<213> ORGANISM: Artificial
<220> FEATURE:
<223> OTHER INFORMATION: Primer

<400> SEQUENCE: 35
gcccgtaaat tgttcgacga aa                           22

<210> SEQ ID NO 36
<211> LENGTH: 22
<212> TYPE: DNA
<213> ORGANISM: Artificial
<220> FEATURE:
<223> OTHER INFORMATION: Primer

<400> SEQUENCE: 36
gtaactcccc aagtcagcat ca                           22

<210> SEQ ID NO 37
<211> LENGTH: 25
<212> TYPE: DNA
<213> ORGANISM: Artificial
<220> FEATURE:
<223> OTHER INFORMATION: Primer

<400> SEQUENCE: 37
ggaatgaatg gagggtatgg atgat                        25

<210> SEQ ID NO 38
<211> LENGTH: 25
<212> TYPE: DNA
<213> ORGANISM: Artificial
<220> FEATURE:
<223> OTHER INFORMATION: Primer

<400> SEQUENCE: 38
gtctctcctc aataacatcc cttca                        25

<210> SEQ ID NO 39
<211> LENGTH: 25
<212> TYPE: DNA
<213> ORGANISM: Artificial
<220> FEATURE:
<223> OTHER INFORMATION: Primer

<400> SEQUENCE: 39
tcaactgtaa aagggttct cgttg                                          25

<210> SEQ ID NO 40
<211> LENGTH: 25
<212> TYPE: DNA
<213> ORGANISM: Artificial
<220> FEATURE:
<223> OTHER INFORMATION: Primer

<400> SEQUENCE: 40
tatcaacact tcttagcttg cctct                                         25

<210> SEQ ID NO 41
<211> LENGTH: 25
<212> TYPE: DNA
<213> ORGANISM: Artificial
<220> FEATURE:
<223> OTHER INFORMATION: Primer

<400> SEQUENCE: 41
taggtatagg gaccaggaaa gagaa                                         25

<210> SEQ ID NO 42
<211> LENGTH: 25
<212> TYPE: DNA
<213> ORGANISM: Artificial
<220> FEATURE:
<223> OTHER INFORMATION: Primer

<400> SEQUENCE: 42
gccatataga tctttaagct tggcc                                         25

<210> SEQ ID NO 43
<211> LENGTH: 25
<212> TYPE: DNA
<213> ORGANISM: Artificial
<220> FEATURE:
<223> OTHER INFORMATION: Primer

<400> SEQUENCE: 43
tctagcctgt attggtgact gtaag                                         25

<210> SEQ ID NO 44
<211> LENGTH: 25
<212> TYPE: DNA
<213> ORGANISM: Artificial
<220> FEATURE:
<223> OTHER INFORMATION: Primer

<400> SEQUENCE: 44
tcagatatag gacaagacgg aaacc                                         25

<210> SEQ ID NO 45
<211> LENGTH: 22
<212> TYPE: DNA
<213> ORGANISM: Artificial
<220> FEATURE:

<223> OTHER INFORMATION: Primer

<400> SEQUENCE: 45
aaatgttggc gttatcttgg cg                                            22

<210> SEQ ID NO 46
<211> LENGTH: 22
<212> TYPE: DNA
<213> ORGANISM: Artificial
<220> FEATURE:
<223> OTHER INFORMATION: Primer

<400> SEQUENCE: 46
attcgtgaag ccagctttct ag                                            22

<210> SEQ ID NO 47
<211> LENGTH: 22
<212> TYPE: DNA
<213> ORGANISM: Artificial
<220> FEATURE:
<223> OTHER INFORMATION: Primer

<400> SEQUENCE: 47
tcagggattt ggatgggaaa ga                                            22

<210> SEQ ID NO 48
<211> LENGTH: 22
<212> TYPE: DNA
<213> ORGANISM: Artificial
<220> FEATURE:
<223> OTHER INFORMATION: Primer

<400> SEQUENCE: 48
ttccatgcct tttaagccag tt                                            22

<210> SEQ ID NO 49
<211> LENGTH: 25
<212> TYPE: DNA
<213> ORGANISM: Artificial
<220> FEATURE:
<223> OTHER INFORMATION: Primer

<400> SEQUENCE: 49
gcatctaaac gagctaaaaa ggtac                                         25

<210> SEQ ID NO 50
<211> LENGTH: 25
<212> TYPE: DNA
<213> ORGANISM: Artificial
<220> FEATURE:
<223> OTHER INFORMATION: Primer

<400> SEQUENCE: 50
ccaaaacgaa gaagtgattg tgttg                                         25

<210> SEQ ID NO 51
<211> LENGTH: 23
<212> TYPE: DNA
<213> ORGANISM: Artificial
<220> FEATURE:
<223> OTHER INFORMATION: Primer

<400> SEQUENCE: 51
tgtccctgtc atcgtatttt gga                                           23

```
<210> SEQ ID NO 52
<211> LENGTH: 22
<212> TYPE: DNA
<213> ORGANISM: Artificial
<220> FEATURE:
<223> OTHER INFORMATION: Primer

<400> SEQUENCE: 52
acatgttcaa tgttaggctg ca                                              22

<210> SEQ ID NO 53
<211> LENGTH: 22
<212> TYPE: DNA
<213> ORGANISM: Artificial
<220> FEATURE:
<223> OTHER INFORMATION: Primer

<400> SEQUENCE: 53
tttcactgtt gttcttccct ga                                              22

<210> SEQ ID NO 54
<211> LENGTH: 21
<212> TYPE: DNA
<213> ORGANISM: Artificial
<220> FEATURE:
<223> OTHER INFORMATION: Primer

<400> SEQUENCE: 54
gtccacagac acggctagaa t                                               21

<210> SEQ ID NO 55
<211> LENGTH: 22
<212> TYPE: DNA
<213> ORGANISM: Artificial
<220> FEATURE:
<223> OTHER INFORMATION: Primer

<400> SEQUENCE: 55
atgaggagag tcagaggaag ct                                              22

<210> SEQ ID NO 56
<211> LENGTH: 22
<212> TYPE: DNA
<213> ORGANISM: Artificial
<220> FEATURE:
<223> OTHER INFORMATION: Primer

<400> SEQUENCE: 56
tcgatcctca gaagcatcat gg                                              22

<210> SEQ ID NO 57
<211> LENGTH: 22
<212> TYPE: DNA
<213> ORGANISM: Artificial
<220> FEATURE:
<223> OTHER INFORMATION: Primer

<400> SEQUENCE: 57
gccataactc tgcccttttgt tc                                             22

<210> SEQ ID NO 58
<211> LENGTH: 22
<212> TYPE: DNA
<213> ORGANISM: Artificial
<220> FEATURE:
<223> OTHER INFORMATION: Primer
```

```
<400> SEQUENCE: 58
cgaacaaatt aaacctgagg ca                                              22

<210> SEQ ID NO 59
<211> LENGTH: 22
<212> TYPE: DNA
<213> ORGANISM: Artificial
<220> FEATURE:
<223> OTHER INFORMATION: Primer

<400> SEQUENCE: 59
caaccaagaa acccttcagc ag                                              22

<210> SEQ ID NO 60
<211> LENGTH: 22
<212> TYPE: DNA
<213> ORGANISM: Artificial
<220> FEATURE:
<223> OTHER INFORMATION: Primer

<400> SEQUENCE: 60
acaaacgatt gggtcatgga ga                                              22

<210> SEQ ID NO 61
<211> LENGTH: 22
<212> TYPE: DNA
<213> ORGANISM: Artificial
<220> FEATURE:
<223> OTHER INFORMATION: Primer

<400> SEQUENCE: 61
ggatcctgct tgtgttttg ct                                               22

<210> SEQ ID NO 62
<211> LENGTH: 22
<212> TYPE: DNA
<213> ORGANISM: Artificial
<220> FEATURE:
<223> OTHER INFORMATION: Primer

<400> SEQUENCE: 62
ctcctctttg gcggttaaga gt                                              22

<210> SEQ ID NO 63
<211> LENGTH: 22
<212> TYPE: DNA
<213> ORGANISM: Artificial
<220> FEATURE:
<223> OTHER INFORMATION: Primer

<400> SEQUENCE: 63
aggctcatcc ttgtgtttct gt                                              22

<210> SEQ ID NO 64
<211> LENGTH: 22
<212> TYPE: DNA
<213> ORGANISM: Artificial
<220> FEATURE:
<223> OTHER INFORMATION: Primer

<400> SEQUENCE: 64
ttgtgtccat gaacatgctc tg                                              22

<210> SEQ ID NO 65
<211> LENGTH: 22
```

```
<212> TYPE: DNA
<213> ORGANISM: Artificial
<220> FEATURE:
<223> OTHER INFORMATION: Primer

<400> SEQUENCE: 65
cagaaggagt ttgtgccaac ag                                              22

<210> SEQ ID NO 66
<211> LENGTH: 22
<212> TYPE: DNA
<213> ORGANISM: Artificial
<220> FEATURE:
<223> OTHER INFORMATION: Primer

<400> SEQUENCE: 66
tctccaccct cattttccca tc                                              22

<210> SEQ ID NO 67
<211> LENGTH: 22
<212> TYPE: DNA
<213> ORGANISM: Artificial
<220> FEATURE:
<223> OTHER INFORMATION: Primer

<400> SEQUENCE: 67
agcagagaga agcaacaaag ga                                              22

<210> SEQ ID NO 68
<211> LENGTH: 22
<212> TYPE: DNA
<213> ORGANISM: Artificial
<220> FEATURE:
<223> OTHER INFORMATION: Primer

<400> SEQUENCE: 68
tctacgcaca agactaagtc ga                                              22

<210> SEQ ID NO 69
<211> LENGTH: 22
<212> TYPE: DNA
<213> ORGANISM: Artificial
<220> FEATURE:
<223> OTHER INFORMATION: Primer

<400> SEQUENCE: 69
cacgatacga gcaaccaaat cc                                              22

<210> SEQ ID NO 70
<211> LENGTH: 22
<212> TYPE: DNA
<213> ORGANISM: Artificial
<220> FEATURE:
<223> OTHER INFORMATION: Primer

<400> SEQUENCE: 70
gttcccactt ctcagagcat ca                                              22

<210> SEQ ID NO 71
<211> LENGTH: 22
<212> TYPE: DNA
<213> ORGANISM: Artificial
<220> FEATURE:
<223> OTHER INFORMATION: Primer

<400> SEQUENCE: 71
```
atgctccaaa ggtacaaggc tt                                           22

<210> SEQ ID NO 72
<211> LENGTH: 22
<212> TYPE: DNA
<213> ORGANISM: Artificial
<220> FEATURE:
<223> OTHER INFORMATION: Primer

<400> SEQUENCE: 72
acacacattt ttgcaactgc ca                                           22

<210> SEQ ID NO 73
<211> LENGTH: 25
<212> TYPE: DNA
<213> ORGANISM: Artificial
<220> FEATURE:
<223> OTHER INFORMATION: Primer

<400> SEQUENCE: 73
aagcagttga tttggtggtg tattc                                        25

<210> SEQ ID NO 74
<211> LENGTH: 25
<212> TYPE: DNA
<213> ORGANISM: Artificial
<220> FEATURE:
<223> OTHER INFORMATION: Primer

<400> SEQUENCE: 74
ccataagagc agcttcaaga atctg                                        25

<210> SEQ ID NO 75
<211> LENGTH: 25
<212> TYPE: DNA
<213> ORGANISM: Artificial
<220> FEATURE:
<223> OTHER INFORMATION: Primer

<400> SEQUENCE: 75
tcagtggtaa gtccgtcttt taact                                        25

<210> SEQ ID NO 76
<211> LENGTH: 24
<212> TYPE: DNA
<213> ORGANISM: Artificial
<220> FEATURE:
<223> OTHER INFORMATION: Primer

<400> SEQUENCE: 76
tggaaaagag agaagatcca cttt                                         24

<210> SEQ ID NO 77
<211> LENGTH: 20
<212> TYPE: DNA
<213> ORGANISM: Solanum lycopersicum L.

<400> SEQUENCE: 77
ccactagatg ataatttacg                                              20

<210> SEQ ID NO 78
<211> LENGTH: 20
<212> TYPE: DNA
<213> ORGANISM: Solanum lycopersicum L.

<400> SEQUENCE: 78
tatttgcaca ttgcgtatga                                          20

<210> SEQ ID NO 79
<211> LENGTH: 23
<212> TYPE: DNA
<213> ORGANISM: Solanum lycopersicum L.

<400> SEQUENCE: 79
gtatgtttaa tgttagggag agg                                      23

<210> SEQ ID NO 80
<211> LENGTH: 23
<212> TYPE: DNA
<213> ORGANISM: Solanum lycopersicum L.

<400> SEQUENCE: 80
acataccata tgttgcccga tgg                                      23

<210> SEQ ID NO 81
<211> LENGTH: 23
<212> TYPE: DNA
<213> ORGANISM: Solanum lycopersicum L.

<400> SEQUENCE: 81
gcttgtggaa gatagtcaat ggg                                      23

<210> SEQ ID NO 82
<211> LENGTH: 23
<212> TYPE: DNA
<213> ORGANISM: Solanum lycopersicum L.

<400> SEQUENCE: 82
ggacagagcc cagagaaaat agg                                      23

<210> SEQ ID NO 83
<211> LENGTH: 23
<212> TYPE: DNA
<213> ORGANISM: Solanum lycopersicum L.

<400> SEQUENCE: 83
atattaatcc cattaaagtg tgg                                      23

<210> SEQ ID NO 84
<211> LENGTH: 23
<212> TYPE: DNA
<213> ORGANISM: Solanum lycopersicum L.

<400> SEQUENCE: 84
gtaacagtca tgtcctttgg tgg                                      23

<210> SEQ ID NO 85
<211> LENGTH: 23
<212> TYPE: DNA
<213> ORGANISM: Solanum lycopersicum L.

<400> SEQUENCE: 85
gggttgataa agctcctaaa tgg                                      23

<210> SEQ ID NO 86
<211> LENGTH: 23
<212> TYPE: DNA
<213> ORGANISM: Solanum lycopersicum L.

<400> SEQUENCE: 86
tgttgcccga tggttgaaag tgg                                                    23

<210> SEQ ID NO 87
<211> LENGTH: 23
<212> TYPE: DNA
<213> ORGANISM: Solanum lycopersicum L.

<400> SEQUENCE: 87
ccactagatg ataatttacg tgg                                                    23

<210> SEQ ID NO 88
<211> LENGTH: 422
<212> TYPE: PRT
<213> ORGANISM: Solanum tuberosum

<400> SEQUENCE: 88

```
Met Ile Gln Cys Val Thr Ile Thr Glu Pro Ala Asp Lys Phe Thr Arg
1               5                   10                  15

Asn Leu Ser Leu Thr Lys Asn Ile Lys Asn Ile Ile Leu Gly Trp Ile
            20                  25                  30

Asn Asn Thr Glu Pro Thr Ser Pro Asn Leu Ala Trp Met Val Pro Ser
        35                  40                  45

Phe Ser Gly Gln Ser Pro Glu Lys Leu Gly Lys Asn Trp Met Glu Tyr
    50                  55                  60

Gln Gly Ile Lys Asn Trp Glu Gly Leu Leu Asp Pro Leu Asp Asp Asn
65                  70                  75                  80

Leu Arg Gly Glu Ile Ile Arg Tyr Gly His Phe Val Glu Ala Ala Tyr
                85                  90                  95

Arg Ala Cys Asn Phe Asp Pro Ser Ser Pro Ser Tyr Ala Met Cys Lys
            100                 105                 110

Tyr Ser Arg Lys Lys Leu Phe His Leu Ser Gly Phe Ser Gly Thr Gly
        115                 120                 125

Tyr Arg Val Ser Lys Tyr Leu Lys Ala Thr Ser Gly Ile Lys Leu Pro
    130                 135                 140

Asn Trp Val Asp Lys Ala Pro Lys Trp Met Ser Lys Gln Ser Ser Trp
145                 150                 155                 160

Ile Gly Tyr Val Ala Ile Cys His Asp Gln Arg Glu Ile Ala Arg Leu
                165                 170                 175

Gly Arg Arg Asp Val Val Ile Ala Leu Arg Gly Thr Ala Thr Cys Leu
            180                 185                 190

Glu Trp Leu Glu Asn Leu Gly Ala Thr Leu Thr Pro Leu Pro Asn Ile
        195                 200                 205

Lys His Thr Cys Ser Thr Ile Cys Cys Pro Met Val Glu Ser Gly Phe
    210                 215                 220

Leu Ser Leu Tyr Thr Ser Lys Ile Asp Ala Gln Gln Ser Leu Gln Asp
225                 230                 235                 240

Met Val Arg Glu Glu Ile Ala Arg Ile Lys Lys Ile Tyr Asp Gly Glu
                245                 250                 255

Thr Leu Ser Phe Thr Ile Ala Gly His Ser Leu Gly Ala Ala Leu Ala
            260                 265                 270

Thr Leu Thr Ala Tyr Asp Ile Lys Gln Phe Phe Arg Asp Ile Pro Leu
        275                 280                 285

Val Thr Val Met Ser Phe Gly Gly Pro Arg Val Gly Asn His Ser Phe
    290                 295                 300
```

```
Arg Tyr His Leu Asp Lys Gln Gly Thr Lys Ile Leu Arg Ile Val Asn
305                 310                 315                 320

Ser Asp Asp Leu Ile Thr Lys Ile Pro Gly Phe Val Ile Asp Asn Asn
                325                 330                 335

Asp Asn Lys Phe Ala Glu Lys Ser Gly His Trp Ile Gln Lys Leu Val
            340                 345                 350

Glu Asp Ser Gln Trp Val Tyr Ala Asp Val Gly Cys Glu Leu Arg Leu
        355                 360                 365

Ser Ser Ser Asp Ser Pro Tyr Phe Asn Gly Ile Asn Ile Ala Thr Cys
370                 375                 380

His Glu Leu Asn Thr Tyr Leu His Leu Val Asn Ser Phe Val Ser Ser
385                 390                 395                 400

Asn Cys Pro Val Arg Ala Thr Ala Lys Lys Ile Met His Lys Ser Asn
                405                 410                 415

Asn Asn Val Lys Cys Thr
            420

<210> SEQ ID NO 89
<211> LENGTH: 440
<212> TYPE: PRT
<213> ORGANISM: Capsicum baccatum

<400> SEQUENCE: 89

Met Gln Ile Leu Ala Pro Lys Asn Ile Glu Asn Leu Ile Leu Gly Trp
1               5                   10                  15

Asn Thr Glu Ala Arg Pro Asn Leu Ala Ser Thr Ser Ala Trp Thr Val
            20                  25                  30

Pro Ser Phe Ser Gly Lys Cys Pro Glu Lys Leu Gly Asn Asn Trp Met
        35                  40                  45

Glu Tyr Gln Gly Ile Lys Asn Trp Glu Gly Leu Leu Asp Pro Leu Asp
    50                  55                  60

Asp Asn Leu Arg Gly Glu Ile Ile Arg Tyr Gly His Phe Val Glu Ala
65                  70                  75                  80

Ala Tyr Arg Ala Cys Asn Phe Asp Pro Ser Ser Pro Ser Tyr Ala Met
                85                  90                  95

Cys Arg Tyr Ser Lys Lys Lys Leu Phe Pro Leu Ser Gly Phe Thr Gly
            100                 105                 110

Thr Gly Tyr Arg Val Ser Lys Tyr Leu Lys Ala Thr Ser Gly Ile Lys
        115                 120                 125

Leu Pro Ser Trp Val Asp Lys Ala Pro Lys Trp Met Ala Lys Gln Ser
130                 135                 140

Ser Trp Ile Gly Tyr Val Ala Ile Cys His Asp Gln Arg Glu Ile Ala
145                 150                 155                 160

Arg Leu Gly Arg Arg Asp Val Val Ile Ala Leu Arg Gly Thr Ala Thr
                165                 170                 175

Cys Leu Glu Trp Leu Glu Asn Leu Arg Ala Thr Leu Thr Pro Ile Leu
            180                 185                 190

Asn Asn Asn Asn Asn Asn Asn Glu Asn Ile Lys Cys Cys Ser Ser Val
        195                 200                 205

Cys Thr Leu Asn Asn Cys Cys Pro Met Val Glu Ser Gly Phe Leu Ser
    210                 215                 220

Leu Tyr Thr Ser Met Met Gly Ala Arg Gln Ser Leu Gln Asn Met Val
225                 230                 235                 240

Arg Asp Glu Ile Ala Arg Ile Lys Lys Thr Tyr Pro Gly Glu Thr Leu
                245                 250                 255
```

```
Ser Phe Thr Ile Ala Gly His Ser Leu Gly Ala Ala Leu Ala Thr Leu
            260                 265                 270

Thr Ala Tyr Asp Ile Lys Gln Ala Phe Lys Glu Ile Pro Leu Val Thr
        275                 280                 285

Val Ile Ser Phe Gly Gly Pro Arg Val Gly Asn His Ser Phe Arg Tyr
    290                 295                 300

His Leu Asp Thr Gln Gly Thr Lys Ile Leu Arg Ile Val Asn Ser Asp
305                 310                 315                 320

Asp Leu Ile Thr Lys Val Pro Gly Phe Val Ile Asp Asn Asn Tyr Asn
                325                 330                 335

Asp Asn Phe Thr Glu Lys Ser Gly His Trp Ile Gln Lys Leu Val Glu
            340                 345                 350

Asp Thr Gln Trp Val Tyr Ala Asp Val Gly Cys Glu Leu Arg Leu Ser
        355                 360                 365

Ser Ser Asp Ser Pro Asn His Asn Gly Ile Asn Ile Ala Ala Cys His
    370                 375                 380

Glu Leu Asn Thr Tyr Leu Gln Leu Val Asn Gly Val Ser Ser Tyr Cys
385                 390                 395                 400

Pro Val Arg Ala Thr Ala Lys Lys Met Met Gln Lys Gly Tyr Asn Val
                405                 410                 415

Lys Arg Leu Leu Ser Leu Phe Leu Asn Ile Ala Val Leu Ile Leu Asn
            420                 425                 430

Leu Asp Glu Phe Asp Leu Asn Ala
            435                 440

<210> SEQ ID NO 90
<211> LENGTH: 446
<212> TYPE: PRT
<213> ORGANISM: Ricinus communis

<400> SEQUENCE: 90

Met Gln Leu Ser Leu Val Pro Pro Val Pro Ser Ser Leu Ser Ser Thr
1               5                   10                  15

Ile Ser Thr His Leu Lys Val Gln Cys Cys Thr Leu Thr Gln Pro Ile
            20                  25                  30

Lys Leu Asp Lys Lys Ser Met Glu Ile Asn Arg Pro Leu Lys Asn Trp
        35                  40                  45

Glu His Leu Leu Asp Pro Val Tyr Asn Asn Ser Thr Ser Ser Cys Ser
    50                  55                  60

Ala Ser Gln Arg Pro Val Lys Leu Gly Ser Lys Trp Met Glu Tyr Gln
65                  70                  75                  80

Gly Ile Arg Asn Trp Glu Gly Leu Leu Asn Pro Leu Asp Asp Asn Leu
                85                  90                  95

Arg Ala Glu Ile Leu Arg Tyr Gly Asn Phe Val Glu Ala Ala Tyr Asn
            100                 105                 110

Ser Phe Asp Phe Asp Pro Ser Pro Ala Tyr Ala Thr Cys Arg Phe
        115                 120                 125

Gln Lys Ser Thr Leu Leu Glu Arg Ser Gly Leu Pro Gln Thr Gly Tyr
    130                 135                 140

Arg Leu Thr Lys His Leu Arg Ala Thr Ser Gly Ile Gln Leu Pro Arg
145                 150                 155                 160

Trp Ile Glu Lys Ala Pro Ser Trp Val Ala Thr Gln Ser Ser Trp Ile
                165                 170                 175

Gly Tyr Val Ala Val Cys Gln Asp Lys Glu Glu Ile Ser Arg Leu Gly
```

```
            180                 185                 190
Arg Arg Asp Val Val Ile Ser Tyr Arg Gly Thr Ala Thr Cys Leu Glu
            195                 200                 205

Trp Leu Glu Asn Leu Arg Ala Thr Leu Ala Asn Ile Pro Asp Ala Asn
        210                 215                 220

Ser Glu Thr Glu Thr Ser Gly Pro Cys Ser Cys Gly Pro Met Val Glu
225                 230                 235                 240

Ser Gly Phe Leu Ser Leu Tyr Thr Ser Arg Thr Ala Met Gly Pro Ser
                245                 250                 255

Leu Gln Glu Met Val Arg Glu Ile Gln Arg Leu Leu Gln Ser Tyr
                260                 265                 270

Gly Asp Glu Pro Leu Ser Leu Thr Ile Thr Gly His Ser Leu Gly Ala
                275                 280                 285

Ala Leu Ala Ile Leu Thr Ala Tyr Asp Ile Lys Thr Thr Phe Arg Ser
            290                 295                 300

Ala Pro Leu Val Thr Val Ile Ser Phe Gly Gly Pro Arg Val Gly Asn
305                 310                 315                 320

Arg Ser Phe Arg Gln His Leu Glu Lys Gln Gly Thr Lys Val Leu Arg
                325                 330                 335

Ile Val Asn Ser Asp Asp Leu Ile Thr Lys Val Pro Gly Phe Val Ile
                340                 345                 350

Asp Gly Asp Asn Asp Asn Glu Asn Glu Val Ile Lys Lys Arg Asp Val
            355                 360                 365

Asn Ile Ala Gly Ile Pro Gly Trp Ile Gln Lys Arg Val Glu Glu Thr
        370                 375                 380

Gln Trp Ala Tyr Ala Glu Val Gly Lys Glu Leu Arg Leu Ser Ser Lys
385                 390                 395                 400

Asp Ser Pro Tyr Ile Asn Ser Val Asn Val Ala Thr Cys His Glu Leu
                405                 410                 415

Lys Thr Tyr Leu His Leu Val Asn Gly Phe Val Ser Ser Cys Pro
                420                 425                 430

Phe Arg Ala Thr Ala Lys Arg Val Leu Ser Lys His Arg Arg
            435                 440                 445

<210> SEQ ID NO 91
<211> LENGTH: 374
<212> TYPE: PRT
<213> ORGANISM: Coffea canephora

<400> SEQUENCE: 91

Met Asp Ile Gln Gly Met Lys Asn Trp Glu Gly Leu Leu Asp Pro Leu
1               5                   10                  15

Asp Asn Asn Leu Arg Gly Glu Ile Ile Arg Tyr Gly His Phe Val Glu
                20                  25                  30

Ala Ala Tyr Arg Ser Cys Glu Phe Glu Pro Ser Ser Pro Ser Tyr Ser
            35                  40                  45

Lys Cys Arg Phe Ser Lys Arg Lys Leu Leu Val Gln Ser Gly Phe Ser
        50                  55                  60

Glu Thr Gly Tyr Arg Ile Thr Glu Asn Leu His Ala Thr Ser Gly Ile
65                  70                  75                  80

Gln Leu Pro Gly Trp Ile Glu Arg Ala Pro Ser Trp Ile Ser Met Arg
                85                  90                  95

Ser Ser Trp Ile Gly Tyr Val Ala Val Cys Gln Asp Lys Arg Val Ile
                100                 105                 110
```

```
Ser Lys Leu Gly Arg Arg Asp Val Ile Ala Leu Arg Gly Thr Val
            115                 120                 125

Thr Cys Leu Glu Trp Leu Glu Asn Leu Arg Ala Thr Leu Thr Pro Leu
130                 135                 140

Ser Asn Asp Asn Ala Ala Ser Glu Val Gly Ala Asn Asp Tyr Ser Ser
145                 150                 155                 160

Cys Pro Met Val Glu Ser Gly Phe Leu Ser Leu Tyr Thr Ser Arg Val
                165                 170                 175

Gly Thr Ser Pro Ser Leu Gln Asp Leu Val Arg Gln Glu Ser Gly Arg
            180                 185                 190

Ile Leu Glu Thr Tyr Gly Asp Glu Pro Leu Ser Phe Thr Ile Thr Gly
        195                 200                 205

His Ser Leu Gly Ala Ala Leu Ala Thr Leu Ala Ala Tyr Asp Ile Lys
    210                 215                 220

Glu Thr Phe Lys Cys Glu Pro Leu Val Thr Val Ile Ser Phe Gly Gly
225                 230                 235                 240

Pro Arg Val Gly Asn Gln Ser Phe Arg Cys His Leu Glu Glu Gln Gly
                245                 250                 255

Thr Lys Val Leu Arg Ile Val Asn Ser Asp Asp Leu Ile Thr Lys Met
            260                 265                 270

Pro Gly Phe Val Ile Asp Asn Asn Glu Asp Asn Leu Thr Lys His Asn
        275                 280                 285

Asn Glu Pro Ala Pro Ala Gly Gln Met Val Lys Leu Leu Ser Trp Ile
    290                 295                 300

Gln Lys Ile Ala Glu Asp Ser Gln Trp Val Tyr Ala Asp Val Gly Cys
305                 310                 315                 320

Glu Leu Arg Leu Ser Ser Arg Asp Ser Pro Tyr Val Asn Gly Phe Asp
                325                 330                 335

Phe Ala Ser Cys His Glu Leu Lys Thr Tyr Leu His Leu Val Asn Gly
            340                 345                 350

Phe Val Ser Ser Asn Cys Pro Ile Arg Ala Thr Ala Arg Lys Leu Met
        355                 360                 365

Asn Lys Ser Leu Val Pro
    370

<210> SEQ ID NO 92
<211> LENGTH: 398
<212> TYPE: PRT
<213> ORGANISM: Solanum melongena

<400> SEQUENCE: 92

Met Lys Leu Ser Phe Lys Ser Leu Pro Pro Cys Thr Ser Lys Glu Asn
1               5                   10                  15

Pro Gln Gln His Thr Leu Gln Cys Val Thr Ile Thr Gln Arg Pro Asp
            20                  25                  30

Lys Phe Thr Arg Asn Leu Asn Leu Lys Thr Ile Lys Asn Leu Ile Leu
        35                  40                  45

Gly Trp Asn Asn Ser Pro Asn Leu Pro Ser Thr Ser Ala Trp Thr Val
    50                  55                  60

Pro Ser Phe Pro Glu Lys Leu Gly Lys Asn Trp Met Gly Tyr Gln Gly
65                  70                  75                  80

Ile Lys Asn Trp Glu Gly Leu Leu Asp Pro Leu Asp Asp Asn Leu Arg
                85                  90                  95

Gly Glu Ile Ile Arg Tyr Gly His Phe Val Glu Ala Ala Tyr Arg Ala
            100                 105                 110
```

```
Cys Asn Phe Asp Pro Ser Ser Pro Ser Tyr Ala Met Cys Lys Tyr Ser
            115                 120                 125

Lys Arg Lys Leu Leu Gln Leu Cys Gly Phe Pro Gly Thr Gly Tyr Arg
        130                 135                 140

Val Ser Lys Tyr Leu Lys Ala Thr Ser Gly Ile Lys Leu Pro Ser Trp
145                 150                 155                 160

Val Asp Lys Val Pro Lys Trp Met Ala Lys Gln Ser Ser Trp Ile Gly
                165                 170                 175

Tyr Val Ala Ile Cys His Asp His Arg Glu Ile Ala Arg Leu Gly Arg
                180                 185                 190

Arg Asp Val Val Ile Ala Leu Arg Gly Thr Ala Thr Cys Leu Glu Trp
                195                 200                 205

Leu Glu Asn Leu Arg Ala Thr Leu Thr Pro Leu Pro Asp Ile Asn Cys
        210                 215                 220

Cys Ser Thr Ile Cys Cys Pro Met Val Glu Ser Gly Phe Leu Ser Leu
225                 230                 235                 240

Tyr Thr Ser Lys Met Asp Ser His His Ser Leu Gln Asp Met Val Arg
                245                 250                 255

Glu Glu Ile Ala Arg Ile Arg Lys Ala Tyr Gln Gly Glu Thr Leu Ser
                260                 265                 270

Phe Thr Ile Ala Gly Ile Val Val Gly Asn Asp Ser Phe Arg Tyr His
        275                 280                 285

Leu Asp Lys Gln Gly Thr Lys Ile Leu Arg Ile Val Asn Ser Asp Asp
        290                 295                 300

Leu Ile Thr Lys Val Pro Gly Phe Val Ile Asp Asn Asn Lys Asp Asn
305                 310                 315                 320

Phe Thr Glu Lys Ser Gly His Trp Met Gln Lys Leu Val Glu Asp Ser
                325                 330                 335

Gln Trp Val Tyr Ala Asp Val Gly Cys Glu Leu Arg Leu Ser Ser Ser
                340                 345                 350

Asp Ser Pro Tyr Leu Asn Gly Ile Asn Ile Ala Ala Cys His Glu Leu
        355                 360                 365

Asn Thr Tyr Leu His Leu Val Asn Gly Phe Val Ser Ser Asn Cys Pro
        370                 375                 380

Val Arg Ala Thr Ala Lys Lys Leu Cys Arg Lys Val Thr Met
385                 390                 395

<210> SEQ ID NO 93
<211> LENGTH: 417
<212> TYPE: PRT
<213> ORGANISM: Cucumis melo

<400> SEQUENCE: 93

Met Arg Val Ala Gln Asn Pro Asn Val Pro Ile Pro Asn His Gln Thr
1               5                   10                  15

Ala Thr Met Arg Lys Pro Val Leu Tyr Lys Thr Lys Leu His Met His
            20                  25                  30

Gly Val Glu Asn Lys Leu Arg Cys Ala Thr Ser Ser Ser Ser Ser Ser
        35                  40                  45

Ser Thr Gly Ala Ser Asp Cys Leu Lys Leu Arg Val Lys Val Gly Lys
    50                  55                  60

Arg Trp Lys Glu Tyr Ala Gly Leu Gly Asn Trp Glu Gly Leu Leu Asp
65              70                  75                  80

Pro Leu Asp Asp Asn Leu Arg Asn Glu Ile Leu Arg Tyr Gly Gln Phe
```

```
                    85                  90                  95
Val Asp Ala Ala Tyr Lys Ser Phe Asp Phe Asp Pro Ser Ser Pro Thr
                100                 105                 110

Tyr Ala Thr Cys Leu His Ser Lys Ala Ser Leu Leu Glu Ser Ser Gly
            115                 120                 125

Leu Pro Ser Thr Gly Tyr Arg Val Ser Lys His Leu Arg Ala Thr Ser
        130                 135                 140

Gly Ile Cys Leu Pro Arg Trp Leu Pro Asn Thr Pro Ser Phe Ser Thr
145                 150                 155                 160

Asn Ser Ser Trp Ile Gly Tyr Val Ala Val Ser Gln Asp Lys His Glu
                165                 170                 175

Ile Ser Arg Leu Gly Arg Arg Asp Val Val Ile Ala Leu Arg Gly Thr
            180                 185                 190

Ala Thr Cys Leu Glu Trp Leu Glu Asn Leu Arg Ala Thr Leu Thr Met
        195                 200                 205

Leu Pro Gly Glu Glu Gly Gly Ala Met Val Glu Ser Gly Phe Leu Ser
    210                 215                 220

Leu Tyr Ser Ser Gly Thr Glu Ser Cys Pro Ser Leu Lys Glu Met Val
225                 230                 235                 240

Arg Glu Glu Ile Gly Arg Ile Leu Gln Ser Tyr Gly Glu Glu Pro Leu
                245                 250                 255

Ser Leu Thr Ile Thr Gly His Ser Leu Gly Ala Ala Leu Ala Thr Leu
            260                 265                 270

Ala Ala Tyr Asp Ile Lys Glu Tyr Phe Lys Thr Ser Ala Pro Met Val
        275                 280                 285

Thr Val Met Ser Phe Gly Gly Pro Arg Val Gly Asn Arg Lys Phe Arg
    290                 295                 300

Gln Arg Leu Glu Glu Gln Gly Thr Lys Val Leu Arg Ile Val Asn Ser
305                 310                 315                 320

Glu Asp Val Ile Thr Lys Leu Pro Gly Phe Val Val Asn Asn Asn Asn
                325                 330                 335

Asn Asn Asn Asn Asn Val Glu Glu Gly Gly Gly Arg Leu Arg Trp Ile
            340                 345                 350

Gln Lys Cys Val Glu Glu Thr Glu Trp Ala Tyr Ser Glu Val Gly Arg
        355                 360                 365

Glu Leu Arg Leu Ser Ser Arg Asp Ser Pro His Leu Asn Arg Ile Asn
    370                 375                 380

Val Ala Thr Cys His His Leu Asn Thr Tyr Leu His Leu Val Asp Gly
385                 390                 395                 400

Phe Val Ser Ser Thr Cys Pro Phe Arg Ala Thr Ala Arg Arg Met Phe
                405                 410                 415

Pro

<210> SEQ ID NO 94
<211> LENGTH: 466
<212> TYPE: PRT
<213> ORGANISM: Cucurbita pepo

<400> SEQUENCE: 94

Met Glu Arg Ser Ser Leu Ala Ser Glu Asp Asp Ala Thr Lys Leu Gly
1               5                   10                  15

Asn Glu Gly Thr Thr Pro Arg Arg Gln Lys Glu Asp Met Gly Glu
                20                  25                  30

Gln Leu Met Gln Arg Arg Gln Arg Ile Asp Gly Val Gly Phe Leu Leu
```

```
                35                  40                  45
His Ser Phe Leu His Phe Gln Leu Ala Met Arg Thr Ser Ile Ser Ile
 50                  55                  60

Ser Leu Gly Phe Val Arg Pro His Leu Pro Val Arg Ser Thr Lys Thr
 65                  70                  75                  80

Lys Cys Arg Val Lys Ala Met His Ser Pro Thr Asn Asn Val Gly Arg
                 85                  90                  95

Lys Trp Thr Glu Tyr Gln Gly Ile Gln Asn Trp Asp Gly Leu Leu Asp
                100                 105                 110

Pro Leu Asp Asp His Leu Arg Lys Glu Ile Leu Arg Tyr Gly Arg Phe
                115                 120                 125

Ile Glu Ala Ala Tyr Asn Ser Phe Glu Phe Asp Ile Thr Ser Pro Phe
                130                 135                 140

Tyr Ala Thr Ser Arg His Ser Lys Ser Ser Leu Leu Asn Gln Ser Gly
145                 150                 155                 160

Leu Ser Gln Thr Gly Tyr Arg Leu Thr Lys Tyr Leu Arg Ala Thr Thr
                165                 170                 175

Ser Ile Gly Leu Pro His Trp Val Glu Lys Ala Ala Asn Ser Ile Ala
                180                 185                 190

Thr Arg Ser Ser Trp Ile Gly Tyr Val Ala Val Cys Glu Asp Lys Lys
                195                 200                 205

Glu Ile Ser Arg Leu Gly Arg Arg Asp Ile Val Ile Ala Tyr Arg Gly
210                 215                 220

Thr Ala Thr Cys Leu Glu Trp Leu Glu Asn Leu Arg Ala Thr Leu Thr
225                 230                 235                 240

Glu Leu Pro Asn Asn Glu Phe Asn Thr Asn Arg Ala Val Ser Arg Pro
                245                 250                 255

Met Val Glu Thr Gly Phe Leu Ser Leu Tyr Ser Ser Arg Ile Ala Arg
                260                 265                 270

Leu Pro Ser Leu Lys Gln Thr Ile Arg Glu Val Arg Arg Leu Leu
                275                 280                 285

Lys Ala Tyr Asp Gly Glu Gln Leu Ser Ile Thr Ile Thr Gly His Ser
290                 295                 300

Leu Gly Ala Ala Val Ala Thr Leu Thr Ala Tyr Asp Ile Asn Val Thr
305                 310                 315                 320

Phe Arg Gln Arg Val Pro Leu Val Thr Val Val Ser Phe Gly Gly Pro
                325                 330                 335

Arg Val Gly Asn Lys Asp Phe Arg Arg Ser Leu Glu Glu Gln Gly Thr
                340                 345                 350

Lys Val Leu Arg Ile Val Asn Ser Gly Asp Val Val Thr Lys Val Pro
                355                 360                 365

Gly Phe Val Ala Asp Asp Gly Met Glu Ala Leu Pro Trp Trp Ala Arg
                370                 375                 380

Gln Cys Met Glu Asn Val Pro Ser Gln Trp Met Tyr Ser Glu Gln Ile
385                 390                 395                 400

Phe Lys Pro Glu Trp Lys Leu Ile Val Gln Cys Pro Leu Asn Asp Met
                405                 410                 415

Val Val Leu Pro Leu Glu Val Glu Gln Ile Pro Leu Pro Ala Gln His
                420                 425                 430

Pro Pro Thr Ile Met Asp Asp Glu Met Pro Ala Ala Glu Ala Lys
                435                 440                 445

Val Pro Leu Ser Ser Met Arg Gly Arg Arg Ile Val Val Lys Asp
450                 455                 460
```

Pro Leu
465

<210> SEQ ID NO 95
<211> LENGTH: 400
<212> TYPE: PRT
<213> ORGANISM: Cucumis sativus

<400> SEQUENCE: 95

Met Arg Lys Pro Ala Leu Tyr Lys Asn Lys Leu His Met His Gly Val
1               5                   10                  15

Glu Asn Lys Leu Arg Cys Ala Thr Ser Ser Ser Ser Ser Ser Ser Thr
            20                  25                  30

Gly Ala Ser Glu Cys Leu Lys Arg Arg Val Lys Val Gly Lys Arg Trp
        35                  40                  45

Lys Glu Tyr Ala Gly Leu Gly Asn Trp Glu Gly Leu Leu Asp Pro Leu
    50                  55                  60

Asp Asp Asn Leu Arg Asn Glu Ile Leu Arg Tyr Gly Gln Phe Val Asp
65                  70                  75                  80

Ala Ala Tyr Lys Ser Phe Asp Phe Asp Pro Ser Ser Pro Thr Tyr Ala
                85                  90                  95

Thr Cys Leu His Ser Lys Ala Ser Leu Leu Glu Ser Ser Gly Leu Pro
            100                 105                 110

Ser Thr Gly Tyr Arg Val Ser Lys His Leu Arg Ala Thr Ser Gly Ile
        115                 120                 125

Cys Leu Pro Arg Trp Leu Arg Asn Ala Pro Ser Ile Ser Thr Asn Ser
130                 135                 140

Ser Trp Ile Gly Tyr Val Ala Val Ser Gln Asp Lys His Glu Ile Ser
145                 150                 155                 160

Arg Leu Gly Arg Arg Asp Val Val Ile Ser Leu Arg Gly Thr Ala Thr
                165                 170                 175

Cys Leu Glu Trp Leu Glu Asn Leu Arg Ala Thr Leu Thr Thr Leu Pro
            180                 185                 190

Gly Glu Glu Gly Gly Ala Met Val Glu Ser Gly Phe Leu Ser Leu Tyr
        195                 200                 205

Ser Ser Arg Thr Glu Ser Tyr Pro Ser Leu Lys Glu Met Val Arg Glu
    210                 215                 220

Glu Ile Gly Arg Leu Leu Gln Ser Tyr Gly Glu Glu Ala Leu Ser Leu
225                 230                 235                 240

Thr Ile Thr Gly His Ser Leu Gly Ala Ala Leu Ala Thr Leu Ala Ala
                245                 250                 255

Tyr Asp Ile Lys Glu Tyr Phe Lys Thr Ser Ala Pro Met Val Thr Val
            260                 265                 270

Met Ser Phe Gly Gly Pro Arg Val Gly Asn Arg Lys Phe Arg Gln Arg
        275                 280                 285

Leu Glu Lys Gln Gly Thr Lys Val Leu Arg Ile Val Asn Ser Glu Asp
    290                 295                 300

Val Ile Thr Lys Leu Pro Gly Phe Val Val Asn Ser Ser Ser Ser
305                 310                 315                 320

Ser Asn Asn Asn Val Glu Glu Gly Gly Gly Arg Leu Arg Trp Ile Gln
                325                 330                 335

Lys Tyr Val Glu Glu Thr Gln Trp Ala Tyr Ser Glu Val Gly Arg Glu
            340                 345                 350

Leu Arg Leu Ser Ser Arg Asp Ser Pro His Leu Asn Arg Ile Asn Val

```
                 355                 360                 365
Ala Thr Cys His His Leu Asn Thr Tyr Leu His Leu Val Asp Gly Phe
            370                 375                 380

Val Ser Ser Thr Cys Pro Phe Arg Ala Thr Ala Arg Arg Met Phe Pro
385                 390                 395                 400

<210> SEQ ID NO 96
<211> LENGTH: 434
<212> TYPE: PRT
<213> ORGANISM: Vitis vinifera

<400> SEQUENCE: 96

Met Arg Leu Ser Leu Lys Pro Leu Gly Pro Cys Ile Val Ser Asn Ser
1               5                   10                  15

Ser Arg Asp Phe Thr Ser Arg Ser Cys Ile Thr Ala Ser Gln Pro Ala
            20                  25                  30

Thr Phe Thr Arg Arg Phe Met Glu Lys Arg Gly Ser Lys Asn Trp Glu
        35                  40                  45

Gly Leu Arg Lys Glu Val Glu Gly Gln Trp Val His Ser Arg Gly Asn
    50                  55                  60

Pro Arg Leu Val Lys Leu Gly Lys Arg Trp Met Glu Tyr Gln Gly Ile
65                  70                  75                  80

Arg Asn Trp Asp Gly Leu Leu Asp Pro Leu Asp Lys Leu Arg Cys
                85                  90                  95

Glu Ile Leu Arg Tyr Gly Asp Phe Val Asp Ala Thr Tyr Lys Ala Phe
            100                 105                 110

Asp Phe Asp Ser Ser Pro Thr Tyr Ala Thr Cys Leu Phe Pro Lys
        115                 120                 125

Asn Phe Ile Leu Asp Gly Ala Gly Leu Pro Asn Thr Gly Tyr Arg Pro
    130                 135                 140

Thr Arg Asn Leu Arg Ala Thr Ser Gly Ile Gln Leu Pro Arg Trp Ile
145                 150                 155                 160

Lys Lys Ala Ser Ser Trp Val Ala Thr Glu Ser Ser Trp Ile Gly Tyr
                165                 170                 175

Val Ala Val Cys Gln Asp Lys Glu Glu Ile Ala Arg Leu Gly Arg Arg
            180                 185                 190

Asp Val Val Ile Ala Tyr Arg Gly Thr Ala Thr Cys Leu Glu Trp Leu
        195                 200                 205

Glu Asn Leu Arg Ala Thr Leu Thr Pro Leu Pro Ser Ala His Ser Asp
    210                 215                 220

Cys Met Val Glu Arg Gly Phe Leu Ser Leu Tyr Thr Ser Arg Thr Ala
225                 230                 235                 240

Thr Ser Pro Ser Leu Gln Asp Leu Val Arg Glu Val Ala Ser Leu
                245                 250                 255

Leu Gln Ser Tyr Gly Asp Glu Pro Leu Ser Leu Thr Ile Thr Gly His
            260                 265                 270

Ser Leu Gly Ala Ala Leu Ala Ile Leu Thr Ala Tyr Asp Ile Lys Thr
        275                 280                 285

Thr Phe Ser Arg Ala Pro Leu Val Thr Val Ser Phe Gly Gly Pro
    290                 295                 300

Arg Val Gly Asn Gly Asn Phe Arg Phe Gln Leu Glu Arg Gln Gly Thr
305                 310                 315                 320

Lys Val Leu Arg Ile Val Asn Ser Asp Asp Leu Ile Thr Lys Val Pro
                325                 330                 335
```

-continued

```
Gly Phe Val Ile Asp Asp Asn Gly Val Ala Gly Asp His Asp Val Arg
            340             345             350

Val Ser Gly Leu Pro Ser Trp Ile Pro Lys Arg Val Val Asp Thr Gln
        355             360             365

Trp Leu Tyr Ala Asp Val Gly Arg Glu Leu Arg Leu Arg Ser Arg Asp
    370             375             380

Ser Pro Tyr Leu Gly Ser Ile Asn Val Ala Thr Cys His Asp Leu Arg
385             390             395             400

Thr Tyr Leu His Leu Val Asp Gly Phe Val Ser Ser Lys Cys Pro Phe
            405             410             415

Arg Pro Met Ile Lys Lys Val Ile Lys Ser Tyr Gly Ala Gln Lys Ile
            420             425             430

Arg Val
```